US006726912B1

(12) United States Patent
Webb et al.

(10) Patent No.: US 6,726,912 B1
(45) Date of Patent: Apr. 27, 2004

(54) PAPILLOMAVIRUS POLYPROTEIN CONSTRUCTS

(75) Inventors: Elizabeth Ann Webb, Eltham (AU); Mary Brigid Margetts, Moonee Ponds (AU); John Cooper Cox, Bullengarook (AU); Ian Frazer, St. Lucia (AU); Nigel Alan John McMillan, Woollongabba (AU); Mark Philip Williams, Annerley (AU); Margaret Bridget Holland Moloney, Essendon (AU); Stirling John Edwards, Coburg (AU)

(73) Assignees: CSL Limited, Parkville (AU); University of Queensland of St. Lucia, Queensland (AU)

( * ) Notice: Subject to any disclaimer, the term of this patent is extended or adjusted under 35 U.S.C. 154(b) by 1 day.

(21) Appl. No.: 10/011,749

(22) Filed: Dec. 11, 2001

Related U.S. Application Data

(62) Division of application No. 09/000,094, filed as application No. PCT/AU96/00473 on Jul. 26, 1996, now Pat. No. 6,365,160.

(30) Foreign Application Priority Data

Jul. 27, 1995 (AU) .......................... PN 4439/95

(51) Int. Cl.$^7$ ........................ A61K 39/12; C12P 19/34
(52) U.S. Cl. ................. 424/199.1; 424/204.1; 424/192.1; 424/186.1; 435/320.1; 435/69.1; 435/91.33
(58) Field of Search ............ 424/199.1, 204.1, 424/192.1, 186.1; 435/370.1, 69.1, 6, 235.1, 91.33; 536/23.72

(56) References Cited

U.S. PATENT DOCUMENTS

| 5,955,087 A | | 9/1999 | Whittle et al. | |
| 6,004,557 A | | 12/1999 | Edwards et al. | |
| 6,123,948 A | * | 9/2000 | Whittle et al. | ........... 424/204.1 |

FOREIGN PATENT DOCUMENTS

| DE | 44 35 907 | 4/1996 |
| WO | WO 92/05248 | 4/1992 |
| WO | WO 92/11290 | 7/1992 |
| WO | WO 92/16636 | 10/1992 |
| WO | WO 94/12629 | 6/1994 |

OTHER PUBLICATIONS

Taniguchi et al., "A Major Transcript of Human Papillomavirus Type 16 in Transformed NIH 3T3 Cells contains Polycistronic MRNA Encoding E7, E5, and E1^E4 Fusion Gene, " *Virus Genes* (1990), vol. 3, No. 3, pp. 221–233.

Rohlfs et al., "Viral Trans. Human Keratinocyte Cell Lines Immortalized by Human Papillomavirus Type–16," *Virology* (1991), vol. 183, pp. 331–342.

Chiang et al., "An E1M^E2C Fusion Protein Encoded by Human Papillomavirus Type 11 is a Sequence–Specific Transcription Repressor," *Journal of Virology* ; (1991), vol. 65, pp. 3317–3329.

Lamberti et al. "Transcriptional Activation by the Papillomabirus E6 Zinc Finger Oncoprotein," *The EMBO Journal* (1990), vol. 9, pp. 1907–1913.

Abstract of WO 96/11272, "Papilloma Virus–Like Particles, Fusion Proteins and Process for Producing the Same, " (Apr. 1996).

Stauffer et al., "Experimentia: 26$^{th}$ Annual Meeting of Swiss Societies for Experimental Biology," XP002101770, Abstract Only, Feb. 1994.

Selvakumar et al, "Immunization with Nonstructural Proteins E1 and E2 of Cottontail Rabbit papillomavirus Stimulates Regression of Virus–Induced Papillomas," *J. of Virology* (Jan. 1995), vol. 69, pp. 602–605.

Meneuzzi et al., "Immunization against Human Papillomavirus Type 16 Tumor Cells with Recombinant Vaccinia Viruses Expressing E6 and E7," *Virology* (1991), Vo. 69, pp. 62–69.

Tomita et al., "Translational Properties of the Human Papillomavirus Type–6L1–Coding mRNA," *Virology* (1991), vol. 183, pp. 331–342.

* cited by examiner

*Primary Examiner*—Ali R. Salimi
(74) *Attorney, Agent, or Firm*—Foley & Lardner

(57) ABSTRACT

A papillomavirus polyprotein construct comprises at least two amino acid sequences fused directly or indirectly together, each of the sequences being the sequence of an early ORF protein of papillomavirus or an immunogenic variant or fragment thereof, and at least one of said sequences being other than the E6 or E7 protein sequence or an immunogenic variant or fragment thereof. Nucleic acid molecules encoding the polyprotein construct, prophylactic or therapeutic compositions comprising the polyprotein construct or the nucleic acid molecule, and methods for eliciting an immune response against papillomavirus in a host animal are also provided.

23 Claims, 12 Drawing Sheets

ANTI-E4 PEPTIDE

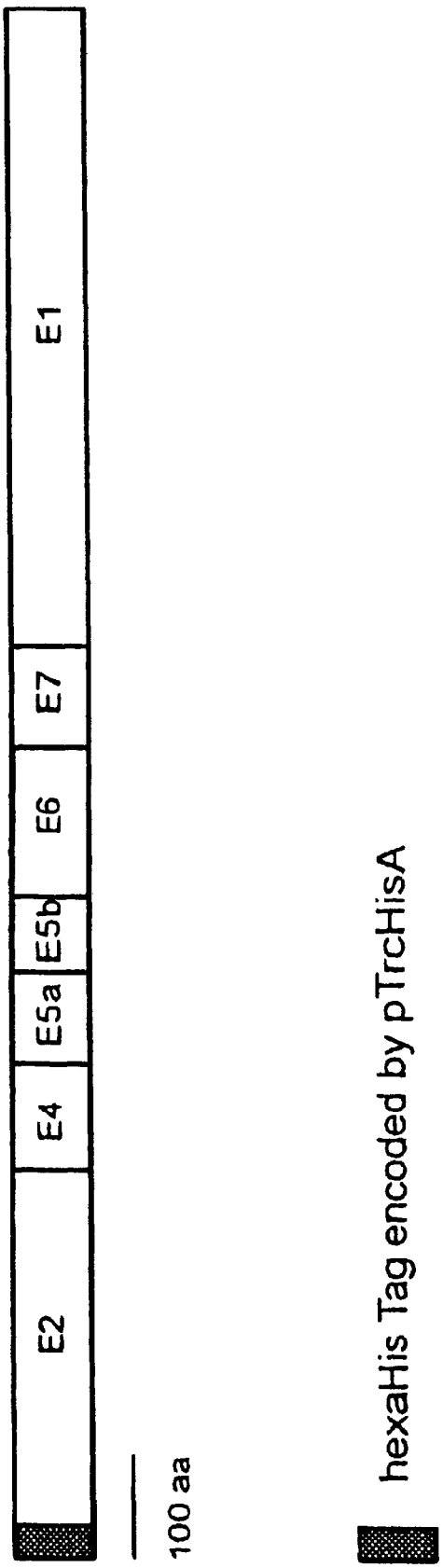

SEQUENCE LISTING (1) GENERAL INFORMATION:

(iii) NUMBER OF SEQUENCES: 50

(2) INFORMATION FOR SEQ ID NO: 1:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 1:

GCGCCCCGGG ATGGAAAGTG CAAATGCCTC                                      30

(2) INFORMATION FOR SEQ ID NO: 2:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 2:

GCGCTCTAGA CCATGGAAGC TTGGGTAACA TGTCTTCCAT GC                        42

(2) INFORMATION FOR SEQ ID NO: 3:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 3:

GCGCTCTAGA GAGCTCGGTA CCACTAGTGG AGCACCAAAC ATTGGGAAG                 49

(2) INFORMATION FOR SEQ ID NO: 4:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 4:

GCGCAGATCT TAGGCGTAGC TGAACTGTTA C                                    31

(2) INFORMATION FOR SEQ ID NO: 5:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 5:

GCGCCCATGG GAAGTGGTGC CTGTACAAAT AGC                                  33

(2) INFORMATION FOR SEQ ID NO: 6:

(i) SEQUENCE CHARACTERISTICS:
            (A) LENGTH: 32 base pairs
            (B) TYPE: nucleic acid
            (C) STRANDEDNESS: single (D) TOPOLOGY: linear (ii) MOLECULE TYPE: DNA (genomic)

(xi) SEQUENCE DESCRIPTION: SEQ ID NO: 6:

GCGCTCTAGA TTGCTGTGTG GTAACAATAT AG                                    32

(2) INFORMATION FOR SEQ ID NO: 7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GCGCAAGCTT CATGGAAGAC ATGTTACCCT AAAG                                  34

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

GCGCCCATGG GGTCTTCGGT GCGCAGATGG                                       30

(2) INFORMATION FOR SEQ ID NO: 9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

GCGCGAGCTC GCGGACGATT CAGGTACAGA AAATG                                 35

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GCGCGGTACC TAAAGTTCTA ACAACTGTTC CTG                                   33

(2) INFORMATION FOR SEQ ID NO: 11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GCGCGGTACC GAAGCAATAG CCAAGCGTTT AG                                         32

(2) INFORMATION FOR SEQ ID NO: 12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

GCGCACTAGT CAATAGGTGC AGTGACATAA ATC                                        33

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GCGCTCTAGA CTAACATGTC AATTTAATGA TG                                         32

(2) INFORMATION FOR SEQ ID NO: 14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GCGCGAGCTC ATTCATATAT ATATAATCAC C                                          31

(2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GCGCCCGGG ATGGAAGCAA TAGCCAAGCG                                             30

(2) INFORMATION FOR SEQ ID NO: 16:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

GCGCTCTAGA CCATGGGGTA CCGAGCTCCA ATAGGTGCAG TGACATAAAT C                    51

(2) INFORMATION FOR SEQ ID NO: 17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
GCGCTCTAGA CTAACATGTC AATTTAATGA TG                        32
```

(2) INFORMATION FOR SEQ ID NO: 18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

```
GCGCAGATCT CTCGAGATTC ATATATATAT AATCAC                    36
```

(2) INFORMATION FOR SEQ ID NO: 19:

(i) SEQUENCE CHARACTERISTICS:
        (A) LENGTH: 1107 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1104

(xi) SEQUENCE DESCRIPTION: SEQ ID NO: 19:

```
ATG GAA AGT GCA AAT GCC TCC ACG TCT GCA ACG ACC ATA GAC CAG TTG      48
Met Glu Ser Ala Asn Ala Ser Thr Ser Ala Thr Thr Ile Asp Gln Leu
 1               5                  10                  15

TGC AAG ACG TTT AAT CTA TCT ATG CAT ACG TTG CAA ATT AAT TGT GTG      96
Cys Lys Thr Phe Asn Leu Ser Met His Thr Leu Gln Ile Asn Cys Val
             20                  25                  30

TTT TGC AAG AAT GCA CTG ACC ACA GCA GAG ATT TAT TCA TAT GCA TAT     144
Phe Cys Lys Asn Ala Leu Thr Thr Ala Glu Ile Tyr Ser Tyr Ala Tyr
         35                  40                  45

AAA CAC CTA AAG GTC CTG TTT CGA GGC GGC TAT CCA TAT GCA GCC TGC     192
Lys His Leu Lys Val Leu Phe Arg Gly Gly Tyr Pro Tyr Ala Ala Cys
     50                  55                  60

GCG TGC TGC CTA GAA TTT CAT GGA AAA ATA AAC CAA TAT AGA CAC TTT     240
Ala Cys Cys Leu Glu Phe His Gly Lys Ile Asn Gln Tyr Arg His Phe
 65                  70                  75                  80

GAT TAT GCT GGA TAT GCA ACA ACA GTT GAA GAA GAA ACT AAA CAA GAC     288
Asp Tyr Ala Gly Tyr Ala Thr Thr Val Glu Glu Glu Thr Lys Gln Asp
                 85                  90                  95

ATC TTA GAC GTG CTA ATT CGG TGC TAC CTG TGT CAC AAA CCG CTG TGT     336
Ile Leu Asp Val Leu Ile Arg Cys Tyr Leu Cys His Lys Pro Leu Cys
            100                 105                 110

GAA GTA GAA AAG GTA AAA CAT ATA CTA ACC AAG GCG CGG TTC ATA AAG     384
Glu Val Glu Lys Val Lys His Ile Leu Thr Lys Ala Arg Phe Ile Lys
        115                 120                 125
```

```
CTA AAT TGT ACG TGG AAG GGT CGC TGC CTA CAC TGC TGG ACA ACA TGC      432
Leu Asn Cys Thr Trp Lys Gly Arg Cys Leu His Cys Trp Thr Thr Cys
        130                 135                 140

ATG GAA GAC ATG TTA CCC AAG CTT CCA TGG GAA GTG GTG CCT GTA CAA      480
Met Glu Asp Met Leu Pro Lys Leu Pro Trp Glu Val Val Pro Val Gln
145                 150                 155                 160

ATA GCT GCA GGA ACA ACC AGC ACA TTC ATA CTG CCT GTT ATA ATT GCA      528
Ile Ala Ala Gly Thr Thr Ser Thr Phe Ile Leu Pro Val Ile Ile Ala
                165                 170                 175

TTT GTT GTA TGT TTT GTT AGC ATC ATA CTT ATT GTA TGG ATA TCT GAG      576
Phe Val Val Cys Phe Val Ser Ile Ile Leu Ile Val Trp Ile Ser Glu
                180                 185                 190

TTT ATT GTG TAC ACA TCT GTG CTA GTA CTA ACA CTG CTT TTA TAT TTA      624
Phe Ile Val Tyr Thr Ser Val Leu Val Leu Thr Leu Leu Leu Tyr Leu
                195                 200                 205

CTA TTG TGG CTG CTA TTA ACA ACC CCC TTG CAA TTT TTC CTA CTA ACT      672
Leu Leu Trp Leu Leu Leu Thr Thr Pro Leu Gln Phe Phe Leu Leu Thr
        210                 215                 220

CTA CTT GTG TGT TAC TGT CCC GCA TTG TAT ATA CAC TAC TAT ATT GTT      720
Leu Leu Val Cys Tyr Cys Pro Ala Leu Tyr Ile His Tyr Tyr Ile Val
225                 230                 235                 240

ACC ACA CAG CAA TCT AGA GAG CTC GGT ACC ACT AAT GGA GCA CCA AAC      768
Thr Thr Gln Gln Ser Arg Glu Leu Gly Thr Thr Asn Gly Ala Pro Asn
                245                 250                 255

ATT GGG AAG TAT GTT ATG GCA GCA CAG TTA TAT GTT CTC CTG CAT CTG      816
Ile Gly Lys Tyr Val Met Ala Ala Gln Leu Tyr Val Leu Leu His Leu
                260                 265                 270

TAT CTA GCA CTA CAC AAG AAG TAT CCA TTC CTG AAT CTA CTA CAT ACA      864
Tyr Leu Ala Leu His Lys Lys Tyr Pro Phe Leu Asn Leu Leu His Thr
        275                 280                 285

CCC CCG CAC AGA CCT CCA CCC TTG TGT CCT CAA GCA CCA AGG AAG ACG      912
Pro Pro His Arg Pro Pro Pro Leu Cys Pro Gln Ala Pro Arg Lys Thr
        290                 295                 300

CAG TGC AAA CGC CGC CTA GGA AAC GAG CAC GAG GAG TCC AAC AGT CCC      960
Gln Cys Lys Arg Arg Leu Gly Asn Glu His Glu Glu Ser Asn Ser Pro
305                 310                 315                 320

CTT GCA ACG CCT TGT GTG TGG CCC ACA TTG GAC CCG TGG ACA GTG GAA     1008
Leu Ala Thr Pro Cys Val Trp Pro Thr Leu Asp Pro Trp Thr Val Glu
                325                 330                 335

ACC ACA ACC TCA TCA CTA ACA ATC ACG ACC AGC ACC AAA GAC GGA ACA     1056
Thr Thr Thr Ser Ser Leu Thr Ile Thr Thr Ser Thr Lys Asp Gly Thr
                340                 345                 350

ACA GTA ACA GTT CAG CTA CGC CTA AGA TCT CAT CAC CAT CAC CAT CAC     1104
Thr Val Thr Val Gln Leu Arg Leu Arg Ser His His His His His His
                355                 360                 365

TAA                                                                 1107
```

(2) INFORMATION FOR SEQ ID NO: 20:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO: 20:

```
Met Glu Ser Ala Asn Ala Ser Thr Ser Ala Thr Thr Ile Asp Gln Leu
 1               5                  10                  15

Cys Lys Thr Phe Asn Leu Ser Met His Thr Leu Gln Ile Asn Cys Val
                20                  25                  30
```

```
Phe Cys Lys Asn Ala Leu Thr Thr Ala Glu Ile Tyr Ser Tyr Ala Tyr
         35                  40                  45
Lys His Leu Lys Val Leu Phe Arg Gly Gly Tyr Pro Tyr Ala Ala Cys
         50                  55                  60
Ala Cys Cys Leu Glu Phe His Gly Lys Ile Asn Gln Tyr Arg His Phe
 65                  70                  75                  80
Asp Tyr Ala Gly Tyr Ala Thr Thr Val Glu Glu Thr Lys Gln Asp
                 85                  90                  95
Ile Leu Asp Val Leu Ile Arg Cys Tyr Leu Cys His Lys Pro Leu Cys
                100                 105                 110
Glu Val Glu Lys Val Lys His Ile Leu Thr Lys Ala Arg Phe Ile Lys
                115                 120                 125
Leu Asn Cys Thr Trp Lys Gly Arg Cys Leu His Cys Trp Thr Thr Cys
        130                 135                 140
Met Glu Asp Met Leu Pro Lys Leu Pro Trp Glu Val Val Pro Val Gln
145                 150                 155                 160
Ile Ala Ala Gly Thr Thr Ser Thr Phe Ile Leu Pro Val Ile Ile Ala
                    165                 170                 175
Phe Val Val Cys Phe Val Ser Ile Ile Leu Ile Val Trp Ile Ser Glu
                180                 185                 190
Phe Ile Val Tyr Thr Ser Val Leu Val Leu Thr Leu Leu Tyr Leu
        195                 200                 205
Leu Leu Trp Leu Leu Leu Thr Thr Pro Leu Gln Phe Phe Leu Leu Thr
        210                 215                 220
Leu Leu Val Cys Tyr Cys Pro Ala Leu Tyr Ile His Tyr Tyr Ile Val
225                 230                 235                 240
Thr Thr Gln Gln Ser Arg Glu Leu Gly Thr Thr Asn Gly Ala Pro Asn
                    245                 250                 255
Ile Gly Lys Tyr Val Met Ala Ala Gln Leu Tyr Val Leu Leu His Leu
                260                 265                 270
Tyr Leu Ala Leu His Lys Lys Tyr Pro Phe Leu Asn Leu Leu His Thr
        275                 280                 285
Pro Pro His Arg Pro Pro Pro Leu Cys Pro Gln Ala Pro Arg Lys Thr
290                 295                 300
Gln Cys Lys Arg Arg Leu Gly Asn Glu His Glu Glu Ser Asn Ser Pro
305                 310                 315                 320
Leu Ala Thr Pro Cys Val Trp Pro Thr Leu Asp Pro Trp Thr Val Glu
                325                 330                 335
Thr Thr Thr Ser Ser Leu Thr Ile Thr Thr Ser Thr Lys Asp Gly Thr
                340                 345                 350
Thr Val Thr Val Gln Leu Arg Leu Arg Ser His His His His His
        355                 360                 365

(2) INFORMATION FOR SEQ ID NO: 21:

(i) SEQUENCE CHARACTERISTICS:
        (A) LENGTH: 1128 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1125
```

(xi) SEQUENCE DESCRIPTION: SEQ ID NO: 21:

```
ATG GAA AGT GCA AAT GCC TCC ACG TCT GCA ACG ACC ATA GAC CAG TTG       48
Met Glu Ser Ala Asn Ala Ser Thr Ser Ala Thr Thr Ile Asp Gln Leu
 1               5                  10                  15

TGC AAG ACG TTT AAT CTA TCT ATG CAT ACG TTG CAA ATT AAT TGT GTG       96
Cys Lys Thr Phe Asn Leu Ser Met His Thr Leu Gln Ile Asn Cys Val
                20                  25                  30

TTT TGC AAG AAT GCA CTG ACC ACA GCA GAG ATT TAT TCA TAT GCA TAT      144
Phe Cys Lys Asn Ala Leu Thr Thr Ala Glu Ile Tyr Ser Tyr Ala Tyr
         35                  40                  45

AAA CAC CTA AAG GTC CTG TTT CGA GGC GGT TAT CCA TAT GCA GCC TGC      192
Lys His Leu Lys Val Leu Phe Arg Gly Gly Tyr Pro Tyr Ala Ala Cys
     50                  55                  60

GCG TGC TGC CTA GAA TTT CAT GGA AAA ATA AAC CAA TAT AGA CAC TTT      240
Ala Cys Cys Leu Glu Phe His Gly Lys Ile Asn Gln Tyr Arg His Phe
 65              70                  75                  80

GAT TAT GCT GGA TAT GCA ACA ACA GTT GAA GAA GAA ACT AAA CAA GAC      288
Asp Tyr Ala Gly Tyr Ala Thr Thr Val Glu Glu Glu Thr Lys Gln Asp
                85                  90                  95

ATC TTA GAC GTG CTA ATT CGG TGC TAC CTG TGT CAC AAA CCG CTG TGT      336
Ile Leu Asp Val Leu Ile Arg Cys Tyr Leu Cys His Lys Pro Leu Cys
            100                 105                 110

GAA GTA GAA AAG GTA AAA CAT ATA CTA ACC AAG GCG CGG TTC ATA AAG      384
Glu Val Glu Lys Val Lys His Ile Leu Thr Lys Ala Arg Phe Ile Lys
        115                 120                 125

CTA AAT TGT ACG TGG AAG GGT CGC TGC CTA CAC TGC TGG ACA ACA TGC      432
Leu Asn Cys Thr Trp Lys Gly Arg Cys Leu His Cys Trp Thr Thr Cys
130                 135                 140

ATG GAA GAC ATG TTA CCC AAG CTT CAT GGA AGA CAT GTT ACC CTA AAG      480
Met Glu Asp Met Leu Pro Lys Leu His Gly Arg His Val Thr Leu Lys
145                 150                 155                 160

GAT ATT GTA TTA GAC CTG CAA CCT CCA GAC CCT GTA GGG TTA CAT TGC      528
Asp Ile Val Leu Asp Leu Gln Pro Pro Asp Pro Val Gly Leu His Cys
                165                 170                 175

TAT GAG CAA TTA GTA GAC AGC TCA GAA GAT GAG GTG GAC GAA GTG GAC      576
Tyr Glu Gln Leu Val Asp Ser Ser Glu Asp Glu Val Asp Glu Val Asp
            180                 185                 190

GGA CAA GAT TCA CAA CCT TTA AAA CAA CAT TTC CAA ATA GTG ACC TGT      624
Gly Gln Asp Ser Gln Pro Leu Lys Gln His Phe Gln Ile Val Thr Cys
        195                 200                 205

TGC TGT GGA TGT GAC AGC AAC GTT CGA CTG GTT GTG CAG TGT ACA GAA      672
Cys Cys Gly Cys Asp Ser Asn Val Arg Leu Val Val Gln Cys Thr Glu
    210                 215                 220

ACA GAC ATC AGA GAA GTG CAA CAG CTT CTG TTG GGA ACA CTA AAC ATA      720
Thr Asp Ile Arg Glu Val Gln Gln Leu Leu Leu Gly Thr Leu Asn Ile
225                 230                 235                 240

GTG TGT CCC ATC TGC GCA CCG AAG ACC CCA TGG TCT AGA GAG CTC GGT      768
Val Cys Pro Ile Cys Ala Pro Lys Thr Pro Trp Ser Arg Glu Leu Gly
                245                 250                 255

ACC ACT AAT GGA GCA CCA AAC ATT GGG AAG TAT GTT ATG GCA GCA CAG      816
Thr Thr Asn Gly Ala Pro Asn Ile Gly Lys Tyr Val Met Ala Ala Gln
            260                 265                 270

TTA TAT GTT CTC CTG CAT CTG TAT CTA GCA CTA CAC AAG AAG TAT CCA      864
Leu Tyr Val Leu Leu His Leu Tyr Leu Ala Leu His Lys Lys Tyr Pro
        275                 280                 285

TTC CTG AAT CTA CTA CAT ACA CCC CCG CAC AGA CCT CCA CCC TTG TGT      912
Phe Leu Asn Leu Leu His Thr Pro Pro His Arg Pro Pro Pro Leu Cys
    290                 295                 300

CCT CAA GCA CCA AGG AAG ACG CAG TGC AAA CGC CGC CTA GGA AAC GAG      960
Pro Gln Ala Pro Arg Lys Thr Gln Cys Lys Arg Arg Leu Gly Asn Glu
```

```
Pro Gln Ala Pro Arg Lys Thr Gln Cys Lys Arg Arg Leu Gly Asn Glu
305                 310                 315                 320

CAC GAG GAG TCC AAC AGT CCC CTT GCA ACG CCT TGT GTG TGG CCC ACA    1008
His Glu Glu Ser Asn Ser Pro Leu Ala Thr Pro Cys Val Trp Pro Thr
                325                 330                 335

TTG GAC CCG TGG ACA GTG GAA ACC ACA ACC TCA TCA CTA ACA ATC ACG    1056
Leu Asp Pro Trp Thr Val Glu Thr Thr Thr Ser Ser Leu Thr Ile Thr
                340                 345                 350

ACC AGC ACC AAA GAC GGA ACA ACA GTA ACA GTT CAG CTA CGC CTA AGA    1104
Thr Ser Thr Lys Asp Gly Thr Thr Val Thr Val Gln Leu Arg Leu Arg
            355                 360                 365

TCT CAT CAC CAT CAC CAT CAC TAA                                    1128
Ser His His His His His His
    370                 375
```

(2) INFORMATION FOR SEQ ID NO: 22:

(i) SEQUENCE CHARACTERISTICS:
        (A) LENGTH: 375 amino acids
        (B) TYPE: amino acid
        (D) TOPOLOGY: linear (ii) MOLECULE TYPE: protein (xi) SEQUENCE DESCRIPTION: SEQ ID NO: 22:

```
Met Glu Ser Ala Asn Ala Ser Thr Ser Ala Thr Thr Ile Asp Gln Leu
1               5                   10                  15

Cys Lys Thr Phe Asn Leu Ser Met His Thr Leu Gln Ile Asn Cys Val
            20                  25                  30

Phe Cys Lys Asn Ala Leu Thr Thr Ala Glu Ile Tyr Ser Tyr Ala Tyr
        35                  40                  45

Lys His Leu Lys Val Leu Phe Arg Gly Gly Tyr Pro Tyr Ala Ala Cys
    50                  55                  60

Ala Cys Cys Leu Glu Phe His Gly Lys Ile Asn Gln Tyr Arg His Phe
65                  70                  75                  80

Asp Tyr Ala Gly Tyr Ala Thr Thr Val Glu Glu Thr Lys Gln Asp
                85                  90                  95

Ile Leu Asp Val Leu Ile Arg Cys Tyr Leu Cys His Lys Pro Leu Cys
            100                 105                 110

Glu Val Glu Lys Val Lys His Ile Leu Thr Lys Ala Arg Phe Ile Lys
        115                 120                 125

Leu Asn Cys Thr Trp Lys Gly Arg Cys Leu His Cys Trp Thr Thr Cys
    130                 135                 140

Met Glu Asp Met Leu Pro Lys Leu His Gly Arg His Val Thr Leu Lys
145                 150                 155                 160

Asp Ile Val Leu Asp Leu Gln Pro Pro Asp Pro Val Gly Leu His Cys
                165                 170                 175

Tyr Glu Gln Leu Val Asp Ser Ser Glu Asp Val Asp Glu Val Asp
            180                 185                 190

Gly Gln Asp Ser Gln Pro Leu Lys Gln His Phe Gln Ile Val Thr Cys
        195                 200                 205

Cys Cys Gly Cys Asp Ser Asn Val Arg Leu Val Gln Cys Thr Glu
    210                 215                 220

Thr Asp Ile Arg Glu Val Gln Gln Leu Leu Leu Gly Thr Leu Asn Ile
225                 230                 235                 240

Val Cys Pro Ile Cys Ala Pro Lys Thr Pro Trp Ser Arg Glu Leu Gly
                245                 250                 255
```

```
Thr Thr Asn Gly Ala Pro Asn Ile Gly Lys Tyr Val Met Ala Ala Gln
            260                 265                 270

Leu Tyr Val Leu Leu His Leu Tyr Leu Ala Leu His Lys Lys Tyr Pro
            275                 280                 285

Phe Leu Asn Leu Leu His Thr Pro Pro His Arg Pro Pro Leu Cys
            290                 295                 300

Pro Gln Ala Pro Arg Lys Thr Gln Cys Lys Arg Arg Leu Gly Asn Glu
305                 310                 315                 320

His Glu Glu Ser Asn Ser Pro Leu Ala Thr Pro Cys Val Trp Pro Thr
                325                 330                 335

Leu Asp Pro Trp Thr Val Glu Thr Thr Thr Ser Ser Leu Thr Ile Thr
            340                 345                 350

Thr Ser Thr Lys Asp Gly Thr Thr Val Thr Val Gln Leu Arg Leu Arg
            355                 360                 365

Ser His His His His His His
370                 375

(2) INFORMATION FOR SEQ ID NO: 23:

(i) SEQUENCE CHARACTERISTICS:
        (A) LENGTH: 1398 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: CDS
         (B) LOCATION: 1..1395

(xi) SEQUENCE DESCRIPTION: SEQ ID NO: 23:

ATG GAA AGT GCA AAT GCC TCC ACG TCT GCA ACG ACC ATA GAC CAG TTG      48
Met Glu Ser Ala Asn Ala Ser Thr Ser Ala Thr Thr Ile Asp Gln Leu
  1               5                  10                  15

TGC AAG ACG TTT AAT CTA TCT ATG CAT ACG TTG CAA ATT AAT TGT GTG     96
Cys Lys Thr Phe Asn Leu Ser Met His Thr Leu Gln Ile Asn Cys Val
             20                  25                  30

TTT TGC AAG AAT GCA CTG ACC ACA GCA GAG ATT TAT TCA TAT GCA TAT    144
Phe Cys Lys Asn Ala Leu Thr Thr Ala Glu Ile Tyr Ser Tyr Ala Tyr
         35                  40                  45

AAA CAC CTA AAG GTC CTG TTT CGA GGC GGC TAT CCA TAT GCA GCC TGC    192
Lys His Leu Lys Val Leu Phe Arg Gly Gly Tyr Pro Tyr Ala Ala Cys
 50                  55                  60

GCG TGC TGC CTA GAA TTT CAT GGA AAA ATA AAC CAA TAT AGA CAC TTT    240
Ala Cys Cys Leu Glu Phe His Gly Lys Ile Asn Gln Tyr Arg His Phe
 65                  70                  75                  80

GAT TAT GCT GGA TAT GCA ACA ACA GTT GAA GAA GAA ACT AAA CAA GAC    288
Asp Tyr Ala Gly Tyr Ala Thr Thr Val Glu Glu Glu Thr Lys Gln Asp
                 85                  90                  95

ATC TTA GAC GTG CTA ATT CGG TGC TAC CTG TGT CAC AAA CCG CTG TGT    336
Ile Leu Asp Val Leu Ile Arg Cys Tyr Leu Cys His Lys Pro Leu Cys
            100                 105                 110

GAA GTA GAA AAG GTA AAA CAT ATA CTA ACC AAG GCG CGG TTC ATA AAG    384
Glu Val Glu Lys Val Lys His Ile Leu Thr Lys Ala Arg Phe Ile Lys
        115                 120                 125

CTA AAT TGT ACG TGG AAG GGT CGC TGC CTA CAC TGC TGG ACA ACA TGC    432
Leu Asn Cys Thr Trp Lys Gly Arg Cys Leu His Cys Trp Thr Thr Cys
    130                 135                 140

ATG GAA GAC ATG TTA CCC AAG CTT CAT GGA AGA CAT GTT ACC CTA AAG    480
Met Glu Asp Met Leu Pro Lys Leu His Gly Arg His Val Thr Leu Lys
```

-continued

| | |
|---|---|
| GAT ATT GTA TTA GAC CTG CAA CCT CCA GAC CCT GTA GGG TTA CAT TGC<br>Asp Ile Val Leu Asp Leu Gln Pro Pro Asp Pro Val Gly Leu His Cys<br>145 150 155 160<br>165 170 175 | 528 |
| TAT GAG CAA TTA GTA GAC AGC TCA GAA GAT GAG GTG GAC GAA GTG GAC<br>Tyr Glu Gln Leu Val Asp Ser Ser Glu Asp Glu Val Asp Glu Val Asp<br>180 185 190 | 576 |
| GGA CAA GAT TCA CAA CCT TTA AAA CAA CAT TTC CAA ATA GTG ACC TGT<br>Gly Gln Asp Ser Gln Pro Leu Lys Gln His Phe Gln Ile Val Thr Cys<br>195 200 205 | 624 |
| TGC TGT GGA TGT GAC AGC AAC GTT CGA CTG GTT GTG CAG TGT ACA GAA<br>Cys Cys Gly Cys Asp Ser Asn Val Arg Leu Val Val Gln Cys Thr Glu<br>210 215 220 | 672 |
| ACA GAC ATC AGA GAA GTG CAA CAG CTT CTG TTG GGA ACA CTA AAC ATA<br>Thr Asp Ile Arg Glu Val Gln Gln Leu Leu Leu Gly Thr Leu Asn Ile<br>225 230 235 240 | 720 |
| GTG TGT CCC ATC TGC GCA CCG AAG ACC CCA TGG GAA GTG GTG CCT GTA<br>Val Cys Pro Ile Cys Ala Pro Lys Thr Pro Trp Glu Val Val Pro Val<br>245 250 255 | 768 |
| CAA ATA GCT GCA GGA ACA ACC AGC ACA TTC ATA CTG CCT GTT ATA ATT<br>Gln Ile Ala Ala Gly Thr Thr Ser Thr Phe Ile Leu Pro Val Ile Ile<br>260 265 270 | 816 |
| GCA TTT GTT GTA TGT TTT GTT AGC ATC ATA CTT ATT GTA TGG ATA TCT<br>Ala Phe Val Val Cys Phe Val Ser Ile Ile Leu Ile Val Trp Ile Ser<br>275 280 285 | 864 |
| GAG TTT ATT GTG TAC ACA TCT GTG CTA GTA CTA ACA CTG CTT TTA TAT<br>Glu Phe Ile Val Tyr Thr Ser Val Leu Val Leu Thr Leu Leu Leu Tyr<br>290 295 300 | 912 |
| TTA CTA TTG TGG CTG CTA TTA ACA ACC CCC TTG CAA TTT TTC CTA CTA<br>Leu Leu Leu Trp Leu Leu Leu Thr Thr Pro Leu Gln Phe Phe Leu Leu<br>305 310 315 320 | 960 |
| ACT CTA CTT GTG TGT TAC TGT CCC GCA TTG TAT ATA CAC TAC TAT ATT<br>Thr Leu Leu Val Cys Tyr Cys Pro Ala Leu Tyr Ile His Tyr Tyr Ile<br>325 330 335 | 1008 |
| GTT ACC ACA CAG CAA TCT AGA GAG CTC GGT ACC ACT AAT GGA GCA CCA<br>Val Thr Thr Gln Gln Ser Arg Glu Leu Gly Thr Thr Asn Gly Ala Pro<br>340 345 350 | 1056 |
| AAC ATT GGG AAG TAT GTT ATG GCA GCA CAG TTA TAT GTT CTC CTG CAT<br>Asn Ile Gly Lys Tyr Val Met Ala Ala Gln Leu Tyr Val Leu Leu His<br>355 360 365 | 1104 |
| CTG TAT CTA GCA CTA CAC AAG AAG TAT CCA TTC CTG AAT CTA CTA CAT<br>Leu Tyr Leu Ala Leu His Lys Lys Tyr Pro Phe Leu Asn Leu Leu His<br>370 375 380 | 1152 |
| ACA CCC CCG CAC AGA CCT CCA CCC TTG TGT CCT CAA GCA CCA AGG AAG<br>Thr Pro Pro His Arg Pro Pro Pro Leu Cys Pro Gln Ala Pro Arg Lys<br>385 390 395 400 | 1200 |
| ACG CAG TGC AAA CGC CGC CTA GGA AAC GAG CAC GAG GAG TCC AAC AGT<br>Thr Gln Cys Lys Arg Arg Leu Gly Asn Glu His Glu Glu Ser Asn Ser<br>405 410 415 | 1248 |
| CCC CTT GCA ACG CCT TGT GTG TGG CCC ACA TTG GAC CCG TGG ACA GTG<br>Pro Leu Ala Thr Pro Cys Val Trp Pro Thr Leu Asp Pro Trp Thr Val<br>420 425 430 | 1296 |
| GAA ACC ACA ACC TCA TCA CTA ACA ATC ACG ACC AGC ACC AAA GAC GGA<br>Glu Thr Thr Thr Ser Ser Leu Thr Ile Thr Thr Ser Thr Lys Asp Gly<br>435 440 445 | 1344 |
| ACA ACA GTA ACA GTT CAG CTA CGC CTA AGA TCT CAT CAC CAT CAC CAT<br>Thr Thr Val Thr Val Gln Leu Arg Leu Arg Ser His His His His His<br>450 455 460 | 1392 |
| CAC TAA | 1398 |

His
465

(2) INFORMATION FOR SEQ ID NO: 24:

(i) SEQUENCE CHARACTERISTICS:
        (A) LENGTH: 465 amino acids
        (B) TYPE: amino acid
        (D) TOPOLOGY: linear (ii) MOLECULE TYPE: protein (xi) SEQUENCE DESCRIPTION: SEQ ID NO: 24:

```
Met Glu Ser Ala Asn Ala Ser Thr Ser Ala Thr Thr Ile Asp Gln Leu
 1               5                  10                  15

Cys Lys Thr Phe Asn Leu Ser Met His Thr Leu Gln Ile Asn Cys Val
                20                  25                  30

Phe Cys Lys Asn Ala Leu Thr Thr Ala Glu Ile Tyr Ser Tyr Ala Tyr
            35                  40                  45

Lys His Leu Lys Val Leu Phe Arg Gly Gly Tyr Pro Tyr Ala Ala Cys
        50                  55                  60

Ala Cys Cys Leu Glu Phe His Gly Lys Ile Asn Gln Tyr Arg His Phe
65                  70                  75                  80

Asp Tyr Ala Gly Tyr Ala Thr Thr Val Glu Glu Thr Lys Gln Asp
                85                  90                  95

Ile Leu Asp Val Leu Ile Arg Cys Tyr Leu Cys His Lys Pro Leu Cys
                100                 105                 110

Glu Val Glu Lys Val Lys His Ile Leu Thr Lys Ala Arg Phe Ile Lys
            115                 120                 125

Leu Asn Cys Thr Trp Lys Gly Arg Cys Leu His Cys Trp Thr Thr Cys
130                 135                 140

Met Glu Asp Met Leu Pro Lys Leu His Gly Arg His Val Thr Leu Lys
145                 150                 155                 160

Asp Ile Val Leu Asp Leu Gln Pro Pro Asp Pro Val Gly Leu His Cys
                165                 170                 175

Tyr Glu Gln Leu Val Asp Ser Ser Glu Asp Glu Val Asp Glu Val Asp
                180                 185                 190

Gly Gln Asp Ser Gln Pro Leu Lys Gln His Phe Gln Ile Val Thr Cys
            195                 200                 205

Cys Cys Gly Cys Asp Ser Asn Val Arg Leu Val Val Gln Cys Thr Glu
        210                 215                 220

Thr Asp Ile Arg Glu Val Gln Gln Leu Leu Gly Thr Leu Asn Ile
225                 230                 235                 240

Val Cys Pro Ile Cys Ala Pro Lys Thr Pro Trp Glu Val Val Pro Val
                245                 250                 255

Gln Ile Ala Ala Gly Thr Thr Ser Thr Phe Ile Leu Pro Val Ile Ile
            260                 265                 270

Ala Phe Val Val Cys Phe Val Ser Ile Ile Leu Ile Val Trp Ile Ser
        275                 280                 285

Glu Phe Ile Val Tyr Thr Ser Val Leu Val Leu Thr Leu Leu Leu Tyr
    290                 295                 300

Leu Leu Leu Trp Leu Leu Leu Thr Thr Pro Leu Gln Phe Phe Leu Leu
305                 310                 315                 320

Thr Leu Leu Val Cys Tyr Cys Pro Ala Leu Tyr Ile His Tyr Tyr Ile
                325                 330                 335

Val Thr Thr Gln Gln Ser Arg Glu Leu Gly Thr Thr Asn Gly Ala Pro
```

```
                   340             345             350
Asn Ile Gly Lys Tyr Val Met Ala Ala Gln Leu Tyr Val Leu Leu His
            355             360             365
Leu Tyr Leu Ala Leu His Lys Lys Tyr Pro Phe Leu Asn Leu Leu His
    370             375             380
Thr Pro Pro His Arg Pro Pro Leu Cys Pro Gln Ala Pro Arg Lys
385             390             395             400
Thr Gln Cys Lys Arg Arg Leu Gly Asn Glu His Glu Ser Asn Ser
            405             410             415
Pro Leu Ala Thr Pro Cys Val Trp Pro Thr Leu Asp Pro Trp Thr Val
                420             425             430
Glu Thr Thr Thr Ser Ser Leu Thr Ile Thr Thr Ser Thr Lys Asp Gly
            435             440             445
Thr Thr Val Thr Val Gln Leu Arg Leu Arg Ser His His His His
    450             455             460
His
465

(2) INFORMATION FOR SEQ ID NO: 25:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..108

(xi) SEQUENCE DESCRIPTION: SEQ ID NO: 25:

GAG GAA GAT GGA AGC AAT AGC CAA GCG TTT AGA TGC GTG CCA GGA ACA      48
Glu Glu Asp Gly Ser Asn Ser Gln Ala Phe Arg Cys Val Pro Gly Thr
  1               5                  10                  15

GTT GTT AGA ACT TTA GGT ACC ACT AAT GGA GCA CCA AAC ATT GGG AAG      96
Val Val Arg Thr Leu Gly Thr Thr Asn Gly Ala Pro Asn Ile Gly Lys
             20                  25                  30

TAT GTT ATG GCA                                                     108
Tyr Val Met Ala
        35

(2) INFORMATION FOR SEQ ID NO: 26:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO: 26:

Glu Glu Asp Gly Ser Asn Ser Gln Ala Phe Arg Cys Val Pro Gly Thr
  1               5                  10                  15

Val Val Arg Thr Leu Gly Thr Thr Asn Gly Ala Pro Asn Ile Gly Lys
             20                  25                  30

Tyr Val Met Ala
        35

(2) INFORMATION FOR SEQ ID NO: 27:
```

(i) SEQUENCE CHARACTERISTICS:
    (A) LENGTH: 102 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..102

(xi) SEQUENCE DESCRIPTION: SEQ ID NO: 27:

```
TGT CCC GCA TTG TAT ATA CAC TAC TAT ATT GTT ACC ACA CAG CAA TCT      48
Cys Pro Ala Leu Tyr Ile His Tyr Tyr Ile Val Thr Thr Gln Gln Ser
 1               5                  10                  15

AGA GAG CTC GCG GAC GAT TCA GGT ACA GAA AAT GAG GGG TCT GGG TGT      96
Arg Glu Leu Ala Asp Asp Ser Gly Thr Glu Asn Glu Gly Ser Gly Cys
             20                  25                  30

ACA GGA                                                             102
Thr Gly
```

(2) INFORMATION FOR SEQ ID NO: 28:

(i) SEQUENCE CHARACTERISTICS:
    (A) LENGTH: 34 amino acids
    (B) TYPE: amino acid
    (D) TOPOLOGY: linear (ii) MOLECULE TYPE: protein (xi) SEQUENCE DESCRIPTION: SEQ ID NO: 28:

```
Cys Pro Ala Leu Tyr Ile His Tyr Tyr Ile Val Thr Thr Gln Gln Ser
 1               5                  10                  15

Arg Glu Leu Ala Asp Asp Ser Gly Thr Glu Asn Glu Gly Ser Gly Cys
             20                  25                  30

Thr Gly
```

(2) INFORMATION FOR SEQ ID NO: 29:

(i) SEQUENCE CHARACTERISTICS:
    (A) LENGTH: 108 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..108

(xi) SEQUENCE DESCRIPTION: SEQ ID NO: 29:

```
TTG GGA ACA CTA AAC ATA GTG TGT CCC ATC TGC GCA CCG AAG ACC CCA      48
Leu Gly Thr Leu Asn Ile Val Cys Pro Ile Cys Ala Pro Lys Thr Pro
 1               5                  10                  15

TGG TCT AGA GAG CTC GCG GAC GAT TCA GGT ACA GAA AAT GAG GGG TCT      96
Trp Ser Arg Glu Leu Ala Asp Asp Ser Gly Thr Glu Asn Glu Gly Ser
             20                  25                  30

GGG TGT ACA GGA                                                     108
Gly Cys Thr Gly
         35
```

(2) INFORMATION FOR SEQ ID NO: 30:

(i) SEQUENCE CHARACTERISTICS:
    (A) LENGTH: 36 amino acids (B) TYPE: amino acid
(D) TOPOLOGY: linear (ii) MOLECULE TYPE: protein (xi) SEQUENCE DESCRIPTION: SEQ ID NO: 30:

```
Leu Gly Thr Leu Asn Ile Val Cys Pro Ile Cys Ala Pro Lys Thr Pro
  1               5                  10                  15
Trp Ser Arg Glu Leu Ala Asp Asp Ser Gly Thr Glu Asn Glu Gly Ser
              20                  25                  30
Gly Cys Thr Gly
          35
```

(2) INFORMATION FOR SEQ ID NO: 31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

GTGTGTGAGC TCATGGAAGC AATAGCCAAG                        30

(2) INFORMATION FOR SEQ ID NO: 32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

GTGTGTGTCG ACCAATAGGT GCAGTGACAT                        30

(2) INFORMATION FOR SEQ ID NO: 33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

GTGTGTGTCG ACATGGGAGC ACCAAACATT                        30

(2) INFORMATION FOR SEQ ID NO: 34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

GTGTGTAGAT CTTAGGCGTA GCTGAACTGT                        30

(2) INFORMATION FOR SEQ ID NO: 35:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 35:

GTGTGTAGAT CTATGGAAGT GGTGCCTGTA                                30

(2) INFORMATION FOR SEQ ID NO: 36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

GTGTGTCTTA AGTTGCTGTG TGGTAACAAT                                30

(2) INFORMATION FOR SEQ ID NO: 37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

GTGTGTCTTA AGATGATGCT AACATGTCAA                                30

(2) INFORMATION FOR SEQ ID NO: 38:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

GTGTGTCCGC GGATTCATAT ATATATAATC                                30

(2) INFORMATION FOR SEQ ID NO: 39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

GTGTGTCCGC GGATGGAAAG TGCAAATGCC                                30

(2) INFORMATION FOR SEQ ID NO: 40:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 40:

GTGTGTGCTA GCGGGTAACA TGTCTTCCTA                                          30

(2) INFORMATION FOR SEQ ID NO: 41:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

GTGTGTGCTA GCATGCATGG AAGACATGTT                                          30

(2) INFORMATION FOR SEQ ID NO: 42:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

GTGTGTCGAT CGGGTCTTCG GTGCGCAGAT                                          30

(2) INFORMATION FOR SEQ ID NO: 43:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

GTGTGTCGAT CGATGGCGGA CGATTCAGGT                                          30

(2) INFORMATION FOR SEQ ID NO: 44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

GTGTGTGGTA CCTCATAAAG TTCTAACAAC                                          30

(2) INFORMATION FOR SEQ ID NO: 45:

(i) SEQUENCE CHARACTERISTICS:
        (A) LENGTH: 4770 base pairs
        (B) TYPE: nucleic acid
        (C) STRANDEDNESS: single
        (D) TOPOLOGY: linear (ii) MOLECULE TYPE: DNA (genomic)

(ix) FEATURE:
  (A) NAME/KEY: CDS
  (B) LOCATION: 1..4761

(xi) SEQUENCE DESCRIPTION: SEQ ID NO: 45:

```
ATG GGG GGT TCT CAT CAT CAT CAT CAT CAT GGT ATG GCT AGC ATG ACT        48
Met Gly Gly Ser His His His His His His Gly Met Ala Ser Met Thr
 1               5                  10                  15

GGT GGA CAG CAA ATG GGT CGG GAT CTG TAC GAC GAT GAC GAT AAG GAT        96
Gly Gly Gln Gln Met Gly Arg Asp Leu Tyr Asp Asp Asp Asp Lys Asp
            20                  25                  30

CGA TGG GGA TCC GAG CTC ATG GAA GCA ATA GCC AAG CGT TTA GAT GCG       144
Arg Trp Gly Ser Glu Leu Met Glu Ala Ile Ala Lys Arg Leu Asp Ala
         35                  40                  45

TGC CAG GAA CAG TTG TTA GAA CTT TAT GAA GAA AAC AGT ACT GAC CTA       192
Cys Gln Glu Gln Leu Leu Glu Leu Tyr Glu Glu Asn Ser Thr Asp Leu
 50                  55                  60

CAC AAA CAT GTA TTG CAT TGG AAA TGC ATG AGA CAT GAA AGT GTA TTA       240
His Lys His Val Leu His Trp Lys Cys Met Arg His Glu Ser Val Leu
 65                  70                  75                  80

TTA TAT AAA GCA AAA CAA ATG GGC CTA AGC CAC ATA GGA ATG CAA GTA       288
Leu Tyr Lys Ala Lys Gln Met Gly Leu Ser His Ile Gly Met Gln Val
             85                  90                  95

GTG CCA CCA TTA AAG GTG TCC GAA GCA AAA GGA CAT AAT GCC ATT GAA       336
Val Pro Pro Leu Lys Val Ser Glu Ala Lys Gly His Asn Ala Ile Glu
            100                 105                 110

ATG CAA ATG CAT TTA GAA TCA TTA TTA AGG ACT GAG TAT AGT ATG GAA       384
Met Gln Met His Leu Glu Ser Leu Leu Arg Thr Glu Tyr Ser Met Glu
        115                 120                 125

CCG TGG ACA TTA CAA GAA ACA AGT TAT GAA ATG TGG CAA ACA CCA CCT       432
Pro Trp Thr Leu Gln Glu Thr Ser Tyr Glu Met Trp Gln Thr Pro Pro
130                 135                 140

AAA CGC TGT TTT AAA AAA CGG GGC AAA ACT GTA GAA GTT AAA TTT GAT       480
Lys Arg Cys Phe Lys Lys Arg Gly Lys Thr Val Glu Val Lys Phe Asp
145                 150                 155                 160

GGC TGT GCA AAC AAT ACA ATG GAT TAT GTG GTA TGG ACA GAT GTG TAT       528
Gly Cys Ala Asn Asn Thr Met Asp Tyr Val Val Trp Thr Asp Val Tyr
                165                 170                 175

GTG CAG GAC AAT GAC ACC TGG GTA AAG GTG CAT AGT ATG GTA GAT GCT       576
Val Gln Asp Asn Asp Thr Trp Val Lys Val His Ser Met Val Asp Ala
            180                 185                 190

AAG GGT ATA TAT TAC ACA TGT GGA CAA TTT AAA ACA TAT TAT GTA AAC       624
Lys Gly Ile Tyr Tyr Thr Cys Gly Gln Phe Lys Thr Tyr Tyr Val Asn
        195                 200                 205

TTT GTA AAA GAG GCA GAA AAG TAT GGG AGC ACC AAA CAT TGG GAA GTA       672
Phe Val Lys Glu Ala Glu Lys Tyr Gly Ser Thr Lys His Trp Glu Val
210                 215                 220

TGT TAT GGC AGC ACA GTT ATA TGT TCT CCT GCA TCT GTA TCT AGC ACT       720
Cys Tyr Gly Ser Thr Val Ile Cys Ser Pro Ala Ser Val Ser Ser Thr
225                 230                 235                 240

ACA CAA GAA GTA TCC ATT CCT GAA TCT ACT ACA TAC ACC CCC GCA CAG       768
Thr Gln Glu Val Ser Ile Pro Glu Ser Thr Thr Tyr Thr Pro Ala Gln
                245                 250                 255

ACC TCC ACC CTT GTG TCC TCA AGC ACC AAG GAA GAC GCA GTG CAA ACG       816
Thr Ser Thr Leu Val Ser Ser Ser Thr Lys Glu Asp Ala Val Gln Thr
            260                 265                 270

CCG CCT AGG AAA CGA GCA CGA GGA GTC CAA CAG TCC CCT TGC AAC GCC       864
Pro Pro Arg Lys Arg Ala Arg Gly Val Gln Gln Ser Pro Cys Asn Ala
        275                 280                 285

TTG TGT GTG GCC CAC ATT GGA CCC GTG GAC AGT GGA AAC CAC AAC CTC       912
```

```
Leu Cys Val Ala His Ile Gly Pro Val Asp Ser Gly Asn His Asn Leu
        290                 295                 300

ATC ACT AAC AAT CAC GAC CAG CAC CAA AGA CGG AAC AAC AGT AAC AGT         960
Ile Thr Asn Asn His Asp Gln His Gln Arg Arg Asn Asn Ser Asn Ser
305                 310                 315                 320

TCA GCT ACG CCT ATA GTG CAA TTT CAA GGT GAA TCC AAT TGT TTA AAG        1008
Ser Ala Thr Pro Ile Val Gln Phe Gln Gly Glu Ser Asn Cys Leu Lys
                325                 330                 335

TGT TTT AGA TAT AGG CTA AAT GAC AGA CAC AGA CAT TTA TTT GAT TTA        1056
Cys Phe Arg Tyr Arg Leu Asn Asp Arg His Arg His Leu Phe Asp Leu
        340                 345                 350

ATA TCA TCA ACG TGG CAC TGG GCC TCC TCA AAG GCA CCA CAT AAA CAT        1104
Ile Ser Ser Thr Trp His Trp Ala Ser Ser Lys Ala Pro His Lys His
        355                 360                 365

GCC ATT GTA ACT GTA ACA TAT GAT AGT GAG GAA CAA AGG CAA CAG TTT        1152
Ala Ile Val Thr Val Thr Tyr Asp Ser Glu Glu Gln Arg Gln Gln Phe
370                 375                 380

TTA GAT GTT GTA AAA ATA CCC CCT ACC ATT AGC CAC AAA CTG GGA TTT        1200
Leu Asp Val Val Lys Ile Pro Pro Thr Ile Ser His Lys Leu Gly Phe
385                 390                 395                 400

ATG TCA CTG CAC CTA TTG GTC GAC ATG GGA GCA CCA AAC ATT GGG AAG        1248
Met Ser Leu His Leu Leu Val Asp Met Gly Ala Pro Asn Ile Gly Lys
                405                 410                 415

TAT GTT ATG GCA GCA CAG TTA TAT GTT CTC CTG CAT CTG TAT CTA GCA        1296
Tyr Val Met Ala Ala Gln Leu Tyr Val Leu Leu His Leu Tyr Leu Ala
        420                 425                 430

CTA CAC AAG AAG TAT CCA TTC CTG AAT CTA CTA CAT ACA CCC CCG CAC        1344
Leu His Lys Lys Tyr Pro Phe Leu Asn Leu Leu His Thr Pro Pro His
        435                 440                 445

AGA CCT CCA CCC TTG TGT CCT CAA GCA CCA AGG AAG ACG CAG TGC AAA        1392
Arg Pro Pro Pro Leu Cys Pro Gln Ala Pro Arg Lys Thr Gln Cys Lys
450                 455                 460

CGC CGC CTA GGA AAC GAG CAC GAG GAG TCC AAC AGT CCC CTT GCA ACG        1440
Arg Arg Leu Gly Asn Glu His Glu Glu Ser Asn Ser Pro Leu Ala Thr
465                 470                 475                 480

CCT TGT GTG TGG CCC ACA TTG GAC CCG TGG ACA GTG GAA ACC ACA ACC        1488
Pro Cys Val Trp Pro Thr Leu Asp Pro Trp Thr Val Glu Thr Thr Thr
                485                 490                 495

TCA TCA CTA ACA ATC ACG ACC AGC ACC AAA GAC GGA ACA ACA GTA ACA        1536
Ser Ser Leu Thr Ile Thr Thr Ser Thr Lys Asp Gly Thr Thr Val Thr
        500                 505                 510

GTT CAG CTA CGC CTA AGA TCT ATG GAA GTG GTG CCT GTA CAA ATA GCT        1584
Val Gln Leu Arg Leu Arg Ser Met Glu Val Val Pro Val Gln Ile Ala
        515                 520                 525

GCA GGA ACA ACC AGC ACA TTC ATA CTG CCT GTT ATA ATT GCA TTT GTT        1632
Ala Gly Thr Thr Ser Thr Phe Ile Leu Pro Val Ile Ile Ala Phe Val
530                 535                 540

GTA TGT TTT GTT AGC ATC ATA CTT ATT GTA TGG ATA TCT GAG TTT ATT        1680
Val Cys Phe Val Ser Ile Ile Leu Ile Val Trp Ile Ser Glu Phe Ile
545                 550                 555                 560

GTG TAC ACA TCT GTG CTA GTA CTA ACA CTG CTT TTA TAT TTA CTA TTG        1728
Val Tyr Thr Ser Val Leu Val Leu Thr Leu Leu Leu Tyr Leu Leu Leu
                565                 570                 575

TGG CTG CTA TTA ACA ACC CCC TTG CAA TTT TTC CTA CTA ACT CTA CTT        1776
Trp Leu Leu Leu Thr Thr Pro Leu Gln Phe Phe Leu Leu Thr Leu Leu
        580                 585                 590

GTG TGT TAC TGT CCC GCA TTG TAT ATA CAC TAC TAT ATT GTT ACC ACA        1824
Val Cys Tyr Cys Pro Ala Leu Tyr Ile His Tyr Tyr Ile Val Thr Thr
        595                 600                 605
```

-continued

```
CAG CAA CTT AAG ATG ATG CTA ACA TGT CAA TTT AAT GAT GGA GAT ACC      1872
Gln Gln Leu Lys Met Met Leu Thr Cys Gln Phe Asn Asp Gly Asp Thr
        610                 615                 620

TGG CTG GGT TTG TGG TTG TTA TGT GCC TTT ATT GTA GGG ATG TTG GGG      1920
Trp Leu Gly Leu Trp Leu Leu Cys Ala Phe Ile Val Gly Met Leu Gly
625                 630                 635                 640

TTA TTA TTG ATG CAC TAT AGA GCT GTA CAA GGG GAT AAA CAC ACC AAA      1968
Leu Leu Leu Met His Tyr Arg Ala Val Gln Gly Asp Lys His Thr Lys
                    645                 650                 655

TGT AAG AAG TGT AAC AAA CAC AAC TGT AAT GAT GAT TAT GTA ACT ATG      2016
Cys Lys Lys Cys Asn Lys His Asn Cys Asn Asp Asp Tyr Val Thr Met
                660                 665                 670

CAT TAT ACT ACT GAT GGT GAT TAT ATA TAT ATG AAT CCG CGG ATG GAA      2064
His Tyr Thr Thr Asp Gly Asp Tyr Ile Tyr Met Asn Pro Arg Met Glu
            675                 680                 685

AGT GCA AAT GCC TCC ACG TCT GCA ACG ACC ATA GAC CAG TTG TGC AAG      2112
Ser Ala Asn Ala Ser Thr Ser Ala Thr Thr Ile Asp Gln Leu Cys Lys
        690                 695                 700

ACG TTT AAT CTA TCT ATG CAT ACG TTG CAA ATT AAT TGT GTG TTT TGC      2160
Thr Phe Asn Leu Ser Met His Thr Leu Gln Ile Asn Cys Val Phe Cys
705                 710                 715                 720

AAG AAT GCA CTG ACC ACA GCA GAG ATT TAT TCA TAT GCA TAT AAA CAC      2208
Lys Asn Ala Leu Thr Thr Ala Glu Ile Tyr Ser Tyr Ala Tyr Lys His
                    725                 730                 735

CTA AAG GTC CTG TTT CGA GGC GGC TAT CCA TAT GCA GCC TGC GCG TGC      2256
Leu Lys Val Leu Phe Arg Gly Gly Tyr Pro Tyr Ala Ala Cys Ala Cys
                740                 745                 750

TGC CTA GAA TTT CAT GGA AAA ATA AAC CAA TAT AGA CAC TTT GAT TAT      2304
Cys Leu Glu Phe His Gly Lys Ile Asn Gln Tyr Arg His Phe Asp Tyr
            755                 760                 765

GCT GGA TAT GCA ACA ACA GTT GAA GAA GAA ACT AAA CAA GAC ATC TTA      2352
Ala Gly Tyr Ala Thr Thr Val Glu Glu Glu Thr Lys Gln Asp Ile Leu
        770                 775                 780

GAC GTG CTA ATT CGG TGC TAC CTG TGT CAC AAA CCG CTG TGT GAA GTA      2400
Asp Val Leu Ile Arg Cys Tyr Leu Cys His Lys Pro Leu Cys Glu Val
785                 790                 795                 800

GAA AAG GTA AAA CAT ATA CTA ACC AAG GCG CGG TTC ATA AAG CTA AAT      2448
Glu Lys Val Lys His Ile Leu Thr Lys Ala Arg Phe Ile Lys Leu Asn
                    805                 810                 815

TGT ACG TGG AAG GGT CGC TGC CTA CAC TGC TGG ACA ACA TGC ATG GAA      2496
Cys Thr Trp Lys Gly Arg Cys Leu His Cys Trp Thr Thr Cys Met Glu
                820                 825                 830

GAC ATG TTA CCC GCT AGC ATG CAT GGA AGA CAT GTT ACC CTA AAG GAT      2544
Asp Met Leu Pro Ala Ser Met His Gly Arg His Val Thr Leu Lys Asp
            835                 840                 845

ATT GTA TTA GAC CTG CAA CCT CCA GAC CCT GTA GGG TTA CAT TGC TAT      2592
Ile Val Leu Asp Leu Gln Pro Pro Asp Pro Val Gly Leu His Cys Tyr
        850                 855                 860

GAG CAA TTA GTA GAC AGC TCA GAA GAT GAG GTG GAC GAA GTG GAC GGA      2640
Glu Gln Leu Val Asp Ser Ser Glu Asp Glu Val Asp Glu Val Asp Gly
865                 870                 875                 880

CAA GAT TCA CAA CCT TTA AAA CAA CAT TTC CAA ATA GTG ACC TGT TGC      2688
Gln Asp Ser Gln Pro Leu Lys Gln His Phe Gln Ile Val Thr Cys Cys
                    885                 890                 895

TGT GGA TGT GAC AGC AAC GTT CGA CTG GTT GTG CAG TGT ACA GAA ACA      2736
Cys Gly Cys Asp Ser Asn Val Arg Leu Val Val Gln Cys Thr Glu Thr
                900                 905                 910

GAC ATC AGA GAA GTG CAA CAG CTT CTG TTG GGA ACA CTA AAC ATA GTG      2784
Asp Ile Arg Glu Val Gln Gln Leu Leu Leu Gly Thr Leu Asn Ile Val
            915                 920                 925
```

```
TGT CCC ATC TGC GCA CCG AAG ACC CGA TCG ATG GCG GAC GAT TCA GGT       2832
Cys Pro Ile Cys Ala Pro Lys Thr Arg Ser Met Ala Asp Asp Ser Gly
    930                 935                 940

ACA GAA AAT GAG GGG TCT GGG TGT ACA GGA TGG TTT ATG GTA GAA GCT       2880
Thr Glu Asn Glu Gly Ser Gly Cys Thr Gly Trp Phe Met Val Glu Ala
945                 950                 955                 960

ATA GTG CAA CAC CCA ACA GGT ACA CAA ATA TCA GAC GAT GAG GAT GAG       2928
Ile Val Gln His Pro Thr Gly Thr Gln Ile Ser Asp Asp Glu Asp Glu
                965                 970                 975

GAG GTG GAG GAC AGT GGG TAT GAC ATG GTG GAC TTT ATT GAT GAC AGC       2976
Glu Val Glu Asp Ser Gly Tyr Asp Met Val Asp Phe Ile Asp Asp Ser
            980                 985                 990

AAT ATT ACA CAC AAT TCA CTG GAA GCA CAG GCA TTG TTT AAC AGG CAG       3024
Asn Ile Thr His Asn Ser Leu Glu Ala Gln Ala Leu Phe Asn Arg Gln
        995                 1000                1005

GAG GCG GAC ACC CAT TAT GCG ACT GTG CAG GAC CTA AAA CGA AAG TAT       3072
Glu Ala Asp Thr His Tyr Ala Thr Val Gln Asp Leu Lys Arg Lys Tyr
    1010                1015                1020

TTA GGT AGT CCA TAT GTT AGT CCT ATA AAC ACT ATA GCC GAG GCA GTG       3120
Leu Gly Ser Pro Tyr Val Ser Pro Ile Asn Thr Ile Ala Glu Ala Val
1025                1030                1035                1040

GAA AGT GAA ATA AGT CCA CGA TTG GAC GCC ATT AAA CTT ACA AGA CAG       3168
Glu Ser Glu Ile Ser Pro Arg Leu Asp Ala Ile Lys Leu Thr Arg Gln
                1045                1050                1055

CCA AAA AAG GTA AAG CGA CGG CTG TTT CAA ACC AGG GAA CTA ACG GAC       3216
Pro Lys Lys Val Lys Arg Arg Leu Phe Gln Thr Arg Glu Leu Thr Asp
            1060                1065                1070

AGT GGA TAT GGC TAT TCT GAA GTG GAA GCT GGA ACG GGA ACG CAG GTA       3264
Ser Gly Tyr Gly Tyr Ser Glu Val Glu Ala Gly Thr Gly Thr Gln Val
        1075                1080                1085

GAG AAA CAT GGC GTA CCG GAA AAT GGG GGA GAT GGT CAG GAA AAG GAC       3312
Glu Lys His Gly Val Pro Glu Asn Gly Gly Asp Gly Gln Glu Lys Asp
    1090                1095                1100

ACA GGA AGG GAC ATA GAG GGG GAG GAA CAT ACA GAG GCG GAA GCG CCC       3360
Thr Gly Arg Asp Ile Glu Gly Glu Glu His Thr Glu Ala Glu Ala Pro
1105                1110                1115                1120

ACA AAC AGT GTA CGG GAG CAT GCA GGC ACA GCA GGA ATA TTG GAA TTG       3408
Thr Asn Ser Val Arg Glu His Ala Gly Thr Ala Gly Ile Leu Glu Leu
                1125                1130                1135

TTA AAA TGT AAA GAT TTA CGG GCA GCA TTA CTT GGT AAG TTT AAA GAA       3456
Leu Lys Cys Lys Asp Leu Arg Ala Ala Leu Leu Gly Lys Phe Lys Glu
            1140                1145                1150

TGC TTT GGG CTG TCT TTT ATA GAT TTA ATT AGG CCA TTT AAA AGT GAT       3504
Cys Phe Gly Leu Ser Phe Ile Asp Leu Ile Arg Pro Phe Lys Ser Asp
        1155                1160                1165

AAA ACA ACA TGT TTA GAT TGG GTG GTA GCA GGG TTT GGT ATA CAT CAT       3552
Lys Thr Thr Cys Leu Asp Trp Val Val Ala Gly Phe Gly Ile His His
    1170                1175                1180

AGC ATA TCA GAG GCA TTT CAA AAA TTA ATT GAG CCA TTA AGT TTA TAT       3600
Ser Ile Ser Glu Ala Phe Gln Lys Leu Ile Glu Pro Leu Ser Leu Tyr
1185                1190                1195                1200

GCA CAT ATA CAA TGG CTA ACA AAT GCA TGG GGA ATG GTA TTG TTA GTA       3648
Ala His Ile Gln Trp Leu Thr Asn Ala Trp Gly Met Val Leu Leu Val
                1205                1210                1215

TTA TTA AGA TTT AAA GTA AAT AAA AGT AGA AGT ACC GTT GCA CGT ACA       3696
Leu Leu Arg Phe Lys Val Asn Lys Ser Arg Ser Thr Val Ala Arg Thr
            1220                1225                1230

CTT GCA ACG CTA TTA AAT ATA CCT GAA AAC CAA ATG TTA ATA GAG CCA       3744
Leu Ala Thr Leu Leu Asn Ile Pro Glu Asn Gln Met Leu Ile Glu Pro
```

-continued

```
           1235                1240                1245
CCA AAA ATA CAA AGT GGT GTT GCA GCC CTG TAT TGG TTT CGT ACA GGT      3792
Pro Lys Ile Gln Ser Gly Val Ala Ala Leu Tyr Trp Phe Arg Thr Gly
    1250                1255                1260

ATA TCA AAT GCC AGT ACA GTT ATA GGG GAA GCA CCA GAA TGG ATA ACA      3840
Ile Ser Asn Ala Ser Thr Val Ile Gly Glu Ala Pro Glu Trp Ile Thr
1265                1270                1275                1280

CGC CAA ACA GTT ATT GAA CAC GGG TTG GCA GAC AGT CAG TTT AAA TTA      3888
Arg Gln Thr Val Ile Glu His Gly Leu Ala Asp Ser Gln Phe Lys Leu
            1285                1290                1295

ACA GAA ATG GTG CAG TGG GCG TAT GAT AAT GAC ATA TGC GAG GAG AGT      3936
Thr Glu Met Val Gln Trp Ala Tyr Asp Asn Asp Ile Cys Glu Glu Ser
                1300                1305                1310

GAA ATT GCA TTT GAA TAT GCA CAA AGG GGA GAT TTT GAT TCT AAT GCA      3984
Glu Ile Ala Phe Glu Tyr Ala Gln Arg Gly Asp Phe Asp Ser Asn Ala
            1315                1320                1325

CGA GCA TTT TTA AAT AGC AAT ATG CAG GCA AAA TAT GTG AAA GAT TGT      4032
Arg Ala Phe Leu Asn Ser Asn Met Gln Ala Lys Tyr Val Lys Asp Cys
    1330                1335                1340

GCA ACT ATG TGT AGA CAT TAT AAA CAT GCA GAA ATG AGG AAG ATG TCT      4080
Ala Thr Met Cys Arg His Tyr Lys His Ala Glu Met Arg Lys Met Ser
1345                1350                1355                1360

ATA AAA CAA TGG ATA AAA CAT AGG GGT TCT AAA ATA GAA GGC ACA GGA      4128
Ile Lys Gln Trp Ile Lys His Arg Gly Ser Lys Ile Glu Gly Thr Gly
            1365                1370                1375

AAT TGG AAA CCA ATT GTA CAA TTC CTA CGA CAT CAA AAT ATA GAA TTC      4176
Asn Trp Lys Pro Ile Val Gln Phe Leu Arg His Gln Asn Ile Glu Phe
        1380                1385                1390

ATT CCT TTT TTA ACT AAA TTT AAA TTA TGG CTG CAC GGT ACG CCA AAA      4224
Ile Pro Phe Leu Thr Lys Phe Lys Leu Trp Leu His Gly Thr Pro Lys
    1395                1400                1405

AAA AAC TGC ATA GCC ATA GTA GGC CCT CCA GAT ACT GGG AAA TCG TAC      4272
Lys Asn Cys Ile Ala Ile Val Gly Pro Pro Asp Thr Gly Lys Ser Tyr
    1410                1415                1420

TTT TGT ATG AGT TTA ATA AGC TTT CTA GGA GGT ACA GTT ATT AGT CAT      4320
Phe Cys Met Ser Leu Ile Ser Phe Leu Gly Gly Thr Val Ile Ser His
1425                1430                1435                1440

GTA AAT TCC AGC AGC CAT TTT TGG TTG CAA CCG TTA GTA GAT GCT AAG      4368
Val Asn Ser Ser Ser His Phe Trp Leu Gln Pro Leu Val Asp Ala Lys
                1445                1450                1455

GTA GCA TTG TTA GAT GAT GCA ACA CAG CCA TGT TGG ATA TAT ATG GAT      4416
Val Ala Leu Leu Asp Asp Ala Thr Gln Pro Cys Trp Ile Tyr Met Asp
            1460                1465                1470

ACA TAT ATG AGA AAT TTG TTA GAT GGT AAT CCT ATG AGT ATT GAC AGA      4464
Thr Tyr Met Arg Asn Leu Leu Asp Gly Asn Pro Met Ser Ile Asp Arg
        1475                1480                1485

AAG CAT AAA GCA TTG ACA TTA ATT AAA TGT CCA CCT CTG CTA GTA ACG      4512
Lys His Lys Ala Leu Thr Leu Ile Lys Cys Pro Pro Leu Leu Val Thr
    1490                1495                1500

TCC AAC ATA GAT ATT ACT AAA GAA GAT AAA TAT AAG TAT TTA CAT ACT      4560
Ser Asn Ile Asp Ile Thr Lys Glu Asp Lys Tyr Lys Tyr Leu His Thr
1505                1510                1515                1520

AGA GTA ACA ACA TTT ACA TTT CCA AAT CCA TTC CCT TTT GAC AGA AAT      4608
Arg Val Thr Thr Phe Thr Phe Pro Asn Pro Phe Pro Phe Asp Arg Asn
                1525                1530                1535

GGG AAT GCA GTG TAT GAA CTG TCA AAT ACA AAC TGG AAA TGT TTT TTT      4656
Gly Asn Ala Val Tyr Glu Leu Ser Asn Thr Asn Trp Lys Cys Phe Phe
            1540                1545                1550

GAA AGA CTG TCG TCA AGC CTA GAC ATT CAG GAT TCT GAG GAC GAG GAA      4704
```

```
Glu Arg Leu Ser Ser Ser Leu Asp Ile Gln Asp Ser Glu Asp Glu Glu
        1555                1560                1565

GAT GGA AGC AAT AGC CAA GCG TTT AGA TGC GTG CCA GGA ACA GTT GTT    4752
Asp Gly Ser Asn Ser Gln Ala Phe Arg Cys Val Pro Gly Thr Val Val
    1570                1575                1580

AGA ACT TTA TGAGGTACC                                              4770
Arg Thr Leu
1585
```

(2) INFORMATION FOR SEQ ID NO: 46:

(i) SEQUENCE CHARACTERISTICS:
        (A) LENGTH: 1587 amino acids
        (B) TYPE: amino acid
        (D) TOPOLOGY: linear (ii) MOLECULE TYPE: protein (xi) SEQUENCE DESCRIPTION: SEQ ID NO: 46:

```
Met Gly Gly Ser His His His His His Gly Met Ala Ser Met Thr
 1               5                  10                  15

Gly Gly Gln Gln Met Gly Arg Asp Leu Tyr Asp Asp Asp Lys Asp
            20                  25                  30

Arg Trp Gly Ser Glu Leu Met Glu Ala Ile Ala Lys Arg Leu Asp Ala
        35                  40                  45

Cys Gln Glu Gln Leu Leu Glu Leu Tyr Glu Glu Asn Ser Thr Asp Leu
 50                  55                  60

His Lys His Val Leu His Trp Lys Cys Met Arg His Glu Ser Val Leu
 65                  70                  75                  80

Leu Tyr Lys Ala Lys Gln Met Gly Leu Ser His Ile Gly Met Gln Val
                85                  90                  95

Val Pro Pro Leu Lys Val Ser Glu Ala Lys Gly His Asn Ala Ile Glu
                100                 105                 110

Met Gln Met His Leu Glu Ser Leu Leu Arg Thr Glu Tyr Ser Met Glu
            115                 120                 125

Pro Trp Thr Leu Gln Glu Thr Ser Tyr Glu Met Trp Gln Thr Pro Pro
        130                 135                 140

Lys Arg Cys Phe Lys Lys Arg Gly Lys Thr Val Glu Val Lys Phe Asp
145                 150                 155                 160

Gly Cys Ala Asn Asn Thr Met Asp Tyr Val Val Trp Thr Asp Val Tyr
                165                 170                 175

Val Gln Asp Asn Asp Thr Trp Val Lys Val His Ser Met Val Asp Ala
            180                 185                 190

Lys Gly Ile Tyr Tyr Thr Cys Gly Gln Phe Lys Thr Tyr Tyr Val Asn
        195                 200                 205

Phe Val Lys Glu Ala Glu Lys Tyr Gly Ser Thr Lys His Trp Glu Val
210                 215                 220

Cys Tyr Gly Ser Thr Val Ile Cys Ser Pro Ala Ser Val Ser Ser Thr
225                 230                 235                 240

Thr Gln Glu Val Ser Ile Pro Glu Ser Thr Thr Tyr Thr Pro Ala Gln
                245                 250                 255

Thr Ser Thr Leu Val Ser Ser Ser Thr Lys Glu Asp Ala Val Gln Thr
            260                 265                 270

Pro Pro Arg Lys Arg Ala Arg Gly Val Gln Gln Ser Pro Cys Asn Ala
        275                 280                 285

Leu Cys Val Ala His Ile Gly Pro Val Asp Ser Gly Asn His Asn Leu
        290                 295                 300
```

-continued

```
Ile Thr Asn Asn His Asp Gln His Gln Arg Arg Asn Asn Ser Asn Ser
305                 310                 315                 320

Ser Ala Thr Pro Ile Val Gln Phe Gln Gly Glu Ser Asn Cys Leu Lys
            325                 330                 335

Cys Phe Arg Tyr Arg Leu Asn Asp Arg His Arg His Leu Phe Asp Leu
            340                 345                 350

Ile Ser Ser Thr Trp His Trp Ala Ser Ser Lys Ala Pro His Lys His
        355                 360                 365

Ala Ile Val Thr Val Thr Tyr Asp Ser Glu Glu Gln Arg Gln Gln Phe
370                 375                 380

Leu Asp Val Val Lys Ile Pro Pro Thr Ile Ser His Lys Leu Gly Phe
385                 390                 395                 400

Met Ser Leu His Leu Leu Val Asp Met Gly Ala Pro Asn Ile Gly Lys
            405                 410                 415

Tyr Val Met Ala Ala Gln Leu Tyr Val Leu Leu His Leu Tyr Leu Ala
            420                 425                 430

Leu His Lys Lys Tyr Pro Phe Leu Asn Leu Leu His Thr Pro Pro His
        435                 440                 445

Arg Pro Pro Leu Cys Pro Gln Ala Pro Arg Lys Thr Gln Cys Lys
450                 455                 460

Arg Arg Leu Gly Asn Glu His Glu Glu Ser Asn Ser Pro Leu Ala Thr
465                 470                 475                 480

Pro Cys Val Trp Pro Thr Leu Asp Pro Trp Thr Val Glu Thr Thr Thr
            485                 490                 495

Ser Ser Leu Thr Ile Thr Thr Ser Thr Lys Asp Gly Thr Thr Val Thr
        500                 505                 510

Val Gln Leu Arg Leu Arg Ser Met Glu Val Val Pro Val Gln Ile Ala
        515                 520                 525

Ala Gly Thr Thr Ser Thr Phe Ile Leu Pro Val Ile Ala Phe Val
        530                 535                 540

Val Cys Phe Val Ser Ile Ile Leu Ile Val Trp Ile Ser Glu Phe Ile
545                 550                 555                 560

Val Tyr Thr Ser Val Leu Val Leu Thr Leu Leu Tyr Leu Leu Leu
            565                 570                 575

Trp Leu Leu Leu Thr Thr Pro Leu Gln Phe Phe Leu Leu Thr Leu Leu
            580                 585                 590

Val Cys Tyr Cys Pro Ala Leu Tyr Ile His Tyr Tyr Ile Val Thr Thr
            595                 600                 605

Gln Gln Leu Lys Met Met Leu Thr Cys Gln Phe Asn Asp Gly Asp Thr
610                 615                 620

Trp Leu Gly Leu Trp Leu Leu Cys Ala Phe Ile Val Gly Met Leu Gly
625                 630                 635                 640

Leu Leu Leu Met His Tyr Arg Ala Val Gln Gly Asp Lys His Thr Lys
            645                 650                 655

Cys Lys Lys Cys Asn Lys His Asn Cys Asn Asp Asp Tyr Val Thr Met
            660                 665                 670

His Tyr Thr Thr Asp Gly Asp Tyr Ile Tyr Met Asn Pro Arg Met Glu
        675                 680                 685

Ser Ala Asn Ala Ser Thr Ser Ala Thr Thr Ile Asp Gln Leu Cys Lys
        690                 695                 700

Thr Phe Asn Leu Ser Met His Thr Leu Gln Ile Asn Cys Val Phe Cys
705                 710                 715                 720
```

-continued

```
Lys Asn Ala Leu Thr Thr Ala Glu Ile Tyr Ser Tyr Ala Tyr Lys His
            725                 730                 735

Leu Lys Val Leu Phe Arg Gly Gly Tyr Pro Tyr Ala Ala Cys Ala Cys
            740                 745                 750

Cys Leu Glu Phe His Gly Lys Ile Asn Gln Tyr Arg His Phe Asp Tyr
            755                 760                 765

Ala Gly Tyr Ala Thr Thr Val Glu Glu Glu Thr Lys Gln Asp Ile Leu
            770                 775                 780

Asp Val Leu Ile Arg Cys Tyr Leu Cys His Lys Pro Leu Cys Glu Val
785                 790                 795                 800

Glu Lys Val Lys His Ile Leu Thr Lys Ala Arg Phe Ile Lys Leu Asn
            805                 810                 815

Cys Thr Trp Lys Gly Arg Cys Leu His Cys Trp Thr Thr Cys Met Glu
            820                 825                 830

Asp Met Leu Pro Ala Ser Met His Gly Arg His Val Thr Leu Lys Asp
            835                 840                 845

Ile Val Leu Asp Leu Gln Pro Pro Asp Pro Val Gly Leu His Cys Tyr
            850                 855                 860

Glu Gln Leu Val Asp Ser Ser Glu Asp Glu Val Asp Glu Val Asp Gly
865                 870                 875                 880

Gln Asp Ser Gln Pro Leu Lys Gln His Phe Gln Ile Val Thr Cys Cys
            885                 890                 895

Cys Gly Cys Asp Ser Asn Val Arg Leu Val Val Gln Cys Thr Glu Thr
            900                 905                 910

Asp Ile Arg Glu Val Gln Gln Leu Leu Leu Gly Thr Leu Asn Ile Val
            915                 920                 925

Cys Pro Ile Cys Ala Pro Lys Thr Arg Ser Met Ala Asp Asp Ser Gly
930                 935                 940

Thr Glu Asn Glu Gly Ser Gly Cys Thr Gly Trp Phe Met Val Glu Ala
945                 950                 955                 960

Ile Val Gln His Pro Thr Gly Thr Gln Ile Ser Asp Asp Glu Asp Glu
            965                 970                 975

Glu Val Glu Asp Ser Gly Tyr Asp Met Val Asp Phe Ile Asp Asp Ser
            980                 985                 990

Asn Ile Thr His Asn Ser Leu Glu Ala Gln Ala Leu Phe Asn Arg Gln
            995                 1000                1005

Glu Ala Asp Thr His Tyr Ala Thr Val Gln Asp Leu Lys Arg Lys Tyr
            1010                1015                1020

Leu Gly Ser Pro Tyr Val Ser Pro Ile Asn Thr Ile Ala Glu Ala Val
1025                1030                1035                1040

Glu Ser Glu Ile Ser Pro Arg Leu Asp Ala Ile Lys Leu Thr Arg Gln
            1045                1050                1055

Pro Lys Lys Val Lys Arg Arg Leu Phe Gln Thr Arg Glu Leu Thr Asp
            1060                1065                1070

Ser Gly Tyr Gly Tyr Ser Glu Val Glu Ala Gly Thr Gly Thr Gln Val
            1075                1080                1085

Glu Lys His Gly Val Pro Glu Asn Gly Gly Asp Gly Gln Glu Lys Asp
            1090                1095                1100

Thr Gly Arg Asp Ile Glu Gly Glu Glu His Thr Glu Ala Glu Ala Pro
1105                1110                1115                1120

Thr Asn Ser Val Arg Glu His Ala Gly Thr Ala Gly Ile Leu Glu Leu
            1125                1130                1135

Leu Lys Cys Lys Asp Leu Arg Ala Ala Leu Leu Gly Lys Phe Lys Glu
```

-continued

```
                1140                1145                1150
Cys Phe Gly Leu Ser Phe Ile Asp Leu Ile Arg Pro Phe Lys Ser Asp
                1155                1160                1165
Lys Thr Thr Cys Leu Asp Trp Val Val Ala Gly Phe Gly Ile His His
                1170                1175                1180
Ser Ile Ser Glu Ala Phe Gln Lys Leu Ile Glu Pro Leu Ser Leu Tyr
1185                1190                1195                1200
Ala His Ile Gln Trp Leu Thr Asn Ala Trp Gly Met Val Leu Leu Val
                1205                1210                1215
Leu Leu Arg Phe Lys Val Asn Lys Ser Arg Ser Thr Val Ala Arg Thr
                1220                1225                1230
Leu Ala Thr Leu Leu Asn Ile Pro Glu Asn Gln Met Leu Ile Glu Pro
                1235                1240                1245
Pro Lys Ile Gln Ser Gly Val Ala Ala Leu Tyr Trp Phe Arg Thr Gly
                1250                1255                1260
Ile Ser Asn Ala Ser Thr Val Ile Gly Glu Ala Pro Glu Trp Ile Thr
1265                1270                1275                1280
Arg Gln Thr Val Ile Glu His Gly Leu Ala Asp Ser Gln Phe Lys Leu
                1285                1290                1295
Thr Glu Met Val Gln Trp Ala Tyr Asp Asn Asp Ile Cys Glu Glu Ser
                1300                1305                1310
Glu Ile Ala Phe Glu Tyr Ala Gln Arg Gly Asp Phe Asp Ser Asn Ala
                1315                1320                1325
Arg Ala Phe Leu Asn Ser Asn Met Gln Ala Lys Tyr Val Lys Asp Cys
                1330                1335                1340
Ala Thr Met Cys Arg His Tyr Lys His Ala Glu Met Arg Lys Met Ser
1345                1350                1355                1360
Ile Lys Gln Trp Ile Lys His Arg Gly Ser Lys Ile Glu Gly Thr Gly
                1365                1370                1375
Asn Trp Lys Pro Ile Val Gln Phe Leu Arg His Gln Asn Ile Glu Phe
                1380                1385                1390
Ile Pro Phe Leu Thr Lys Phe Lys Leu Trp Leu His Gly Thr Pro Lys
                1395                1400                1405
Lys Asn Cys Ile Ala Ile Val Gly Pro Pro Asp Thr Gly Lys Ser Tyr
                1410                1415                1420
Phe Cys Met Ser Leu Ile Ser Phe Leu Gly Gly Thr Val Ile Ser His
1425                1430                1435                1440
Val Asn Ser Ser Ser His Phe Trp Leu Gln Pro Leu Val Asp Ala Lys
                1445                1450                1455
Val Ala Leu Leu Asp Asp Ala Thr Gln Pro Cys Trp Ile Tyr Met Asp
                1460                1465                1470
Thr Tyr Met Arg Asn Leu Leu Asp Gly Asn Pro Met Ser Ile Asp Arg
                1475                1480                1485
Lys His Lys Ala Leu Thr Leu Ile Lys Cys Pro Pro Leu Leu Val Thr
                1490                1495                1500
Ser Asn Ile Asp Ile Thr Lys Glu Asp Lys Tyr Lys Tyr Leu His Thr
1505                1510                1515                1520
Arg Val Thr Thr Phe Thr Phe Pro Asn Pro Phe Pro Phe Asp Arg Asn
                1525                1530                1535
Gly Asn Ala Val Tyr Glu Leu Ser Asn Thr Asn Trp Lys Cys Phe Phe
                1540                1545                1550
Glu Arg Leu Ser Ser Ser Leu Asp Ile Gln Asp Ser Glu Asp Glu Glu
                1555                1560                1565
```

```
Asp Gly Ser Asn Ser Gln Ala Phe Arg Cys Val Pro Gly Thr Val Val
    1570                1575                1580

Arg Thr Leu
1585

(2) INFORMATION FOR SEQ ID NO: 47:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 47:

His His His His His His
1               5

(2) INFORMATION FOR SEQ ID NO: 48:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 48:

Leu Gly Asn Glu His Glu Glu Ser Asn Ser Pro Leu Ala Thr Pro Cys
1               5                   10                  15

Val Trp Pro Thr
            20

(2) INFORMATION FOR SEQ ID NO: 49:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 49:

Gln Tyr Arg His Phe Asp Tyr Ala Gln Tyr Ala Thr Thr Val Glu Glu
1               5                   10                  15

Glu Thr Lys Gln Asp Ile Leu Asp
            20

(2) INFORMATION FOR SEQ ID NO: 50:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 50:

Met His Gly Arg His Val Thr Leu Lys Asp Ile Val Leu Asp Leu Gln
1               5                   10                  15

Pro Pro Asp
```

PAPILLOMAVIRUS POLYPROTEIN CONSTRUCTS

CROSS REFERENCE TO RELATED APPLICATIONS

Figure 1:
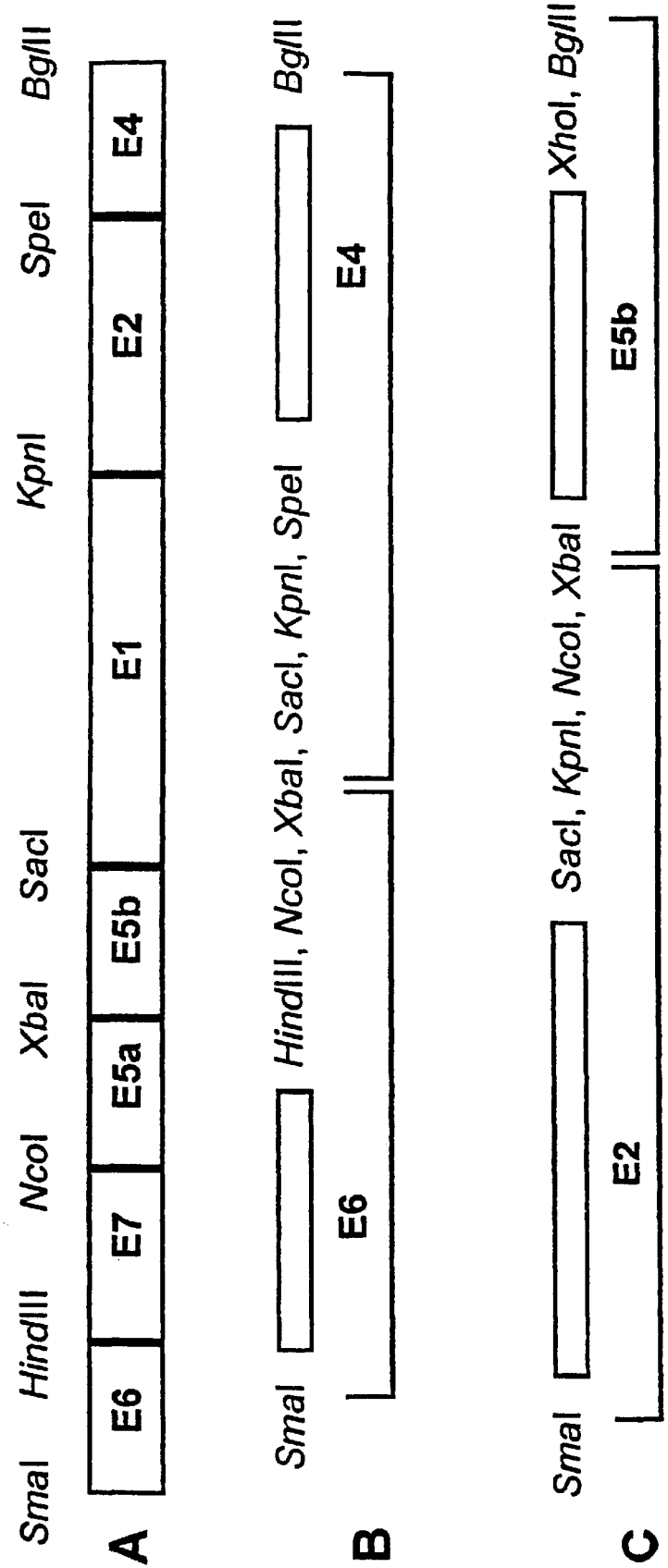

This application is a divisional of U.S. application Ser. No. 09/000,094, filed Apr. 21, 1998, now U.S. Pat. No. 6,365,160, which is a 371 of PCT/AU96/00473, filed Jul. 26, 1996, and which in turn, claims priority to Australian Patent No. 4439/95, filed Jul. 27, 1995.

FIELD OF THE INVENTION

This invention relates to polyprotein constructs and in particular polyprotein constructs comprising a plurality of papillomavirus (PV) amino acid sequences which may be used in compositions for eliciting an immune response against PV, and particularly human papillomavirus (HPV), in, a host animal.

BACKGROUND OF THE INVENTION

Papillomaviruses induce benign hyperproliferative lesions in humans and in many animal species, some of which undergo malignant conversion. The biology of papillomavirus infection is summarised in a review by J. P. Sundberg, entitled "Papillomavirus Infections in Animals" In "Papillomaviruses and Human Disease" edited by K. Syrjanen, L. Gissmann and L. G. Koss, Springer Verlag (1987).

Papillomaviruses are a family of small DNA viruses encoding up to eight early (E1, E2, E3, E4, E5, E6, E7 and E8) and two late genes (L1 and L2). These viruses have been classified in several distinct groups such as HPV which are differentiated into types 1 to~70 depending upon DNA sequence homology. A clinicopathological grouping of HPV and the malignant potential of the lesions with which they are most frequently associated are summarised in "Papillomaviruses and Human Cancer" by H. Pfister, CRC Press, Inc. (1990). For example, HPV type 1 (HPV-1) is present in plantar warts, HPV-6 or HPV-11 are associated with condylomata acuminata (anogenital warts), and HPV-16 or HPV-18 are common in pre-malignant and malignant lesions of the cervical squamous epithelium.

The immunological approach to the prevention of HPV disease requires a thorough analysis of the viral proteins against which humoral and cellular immune responses are mounted during and after infection. However, despite recent limited success (Kreider et al., 1986, *J. Virol.*, 59, 369; Sterling et al., 1990, *J. Virol.*, 64, 6305; Meyers et al., 1992, *Science*, 257, 971; Dollard et al., 1992, *Genes and Development*, 6, 1131), papillomaviruses are notoriously refractory to growth in cultured cells (Teichaman and LaPorta, 1987 In "The Papovaviridae", Vol 2 edited by N. P. Salzman and P. M. Howley, p.109). As a consequence, the lack of viral reagents has delayed the analysis of the immune response to PV infection.

The recent advent of recombinant expression systems in vitro has allowed the production of viral proteins encoded by both early and late genes in relatively large amounts and in a purified form (Tindle et al., 1990, *J. Gen. Virol.*, 71, 1347; Jarrett et al., 1991, *Virology*, 184, 33; Ghim etal., 1992, *Virology*, 190, 548; Stacey etal., 1991, *J. Gen. Virol.*, 73, 2337). These systems have, for the first time, allowed the analysis of the host immune response to these viral proteins.

Interest in immune responses to the non-structural early open reading frame (ORF) proteins of HPV has centred on HPV-16 E7 because of an apparent association between serum antibodies to this protein and cervical cancer (for a review, see "Immune Response to Human Papillomaviruses and the Prospects of Human Papillomavirus-Specific Immunisation" by Tindle and Frazer In "Human Pathogenic Papillomaviruses" edited by H. zur Hausen, Current Topics in Microbioiogy Immunology, 186, Springer-Verlag, Berlin, 1994).

The immune responses to other HPV early ORF proteins have also been investigated including HPV-16 E6 (Stacey et al., 1992, *J. Cen. Virol.*, 73, 2337; Bleul et al., 1991, *J. Clin. Microbiol.*, 29, 1579; Dillner, 1990, *Int. J. Cancer*, 46, 703; and Mülleretal., 1992, *Virology*, 187,508), HPV-16 E2 (Dillner et al., 1989 *Proc. Natl. Acad. Sci. USA*, 86, 3838; Dillner, 1990, supra; Lehtinen et al., 1992, *J. Med. Virol.*, 37, 180; Mann et al., 1990, *Cancer Res.*, 50, 7815; and Jenison et al., 1990, *J. Infect. Dis.*, 162, 60) and HPV-16 E4 (Köchel et al., 1991, *Int. J. Cancer*, 48, 682; Jochmnus-Kudielka et al., 1989, *JNCI*, 81, 1698; and Barber et al., 1992, *Cancer Immunol. immunother.*, 35, 33). However, comparison of these studies reveals a lack of correlation between the results of the various assays which have been used in assessing HPV early ORF protein reactivity in serum (Tindle and Frazer, 1994, supra).

In addition, antibodies to other HPV early ORF proteins have not yet been sought with sufficient rigour in large enough numbers of patients to determine their utility as disease markers or as indicators of HPV protein immunogenicity following HPV infection.

A problem associated with immunising animals with preparations of individual PV proteins is that most of these proteins are comparatively small and might therefore not comprise many reactive epitopes. In addition, immunodominance of particular B or T cell epitopes within a single PV protein would vary presumably between animals of different major histocompatibility (MHC) backgrounds. To this end, the efficacy of such immunogens, in respect of eliciting an immune response against PV, might be expected to differ between animals of diverse MHC background.

In addition, there is surprisingly little knowledge regarding which PV proteins are expressed by infected cells at various stages of differentiation, and hence it is not possible to predict which proteins will be responsible for defining appropriate immunological targets.

The present invention provides a polyprotein construct comprising a plurality of PV early ORF proteins in one fused or linked construct to improve the efficacy of immune stimulation against PV infection and to avoid the need to define specific immunological targets.

SUMMARY OF THE INVENTION

In one aspect, the present invention provides as an isolated product, a polyprotein construct comprising at least two amino acid sequences fused directly or indirectly together, each of said sequences being the sequence of an early open reading frame (ORF) protein of papillomavirus (PV) or an immunogenic variant or fragment thereof, and at least one of said sequences being other than the E6 or E7 protein sequence or an immunogenic variant or fragment thereof.

In yet another aspect, the present invention provides a composition for eliciting a humoral and/or cellular immune response against PV in a host animal, said composition comprising an immunologically effective amount of a construct as described above, together with a pharmaceutically acceptable carrier and/or diluent.

In yet another aspect, this invention provides a method for eliciting a humoral and/or cellular response against PV in a host animal, which method comprises administering to the host animal an immunologically effective amount of a polyprotein construct as described above. In a related aspect, the invention also extends to use of such a polyprotein construct in eliciting an immune response against PV in a host animal. Preferably, the host animal is a human, however the host animal may also be a non-human mammal.

The present invention also extends to a nucleic acid molecule which encodes a polypeptide construct as broadly described above. Such a nucleic acid molecule may be delivered to a host animal in a nucleic acid vaccine composition with a pharmaceutically acceptable carrier and/or diluent, for expression of the encoded polyprotein construct in vivo in a host animal. Alternatively, the nucleic acid molecule may be included in a recombinant DNA molecule comprising an expression control sequence operatively linked to the nucleic acid molecule.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers."

DETAILED DESCRIPTION OF THE INVENTION

The term "polyprotein construct" as used herein is used to describe a protein construct made up of individual proteins that have been joined together in a sequence whereby they retain their original relevant biological activities.

The term "isolated" as used herein denotes that the polyprotein construct has undergone at least one purification or isolation step, and preferably is in a form suitable for administration to a host animal.

By use of the term "immunologically effective amount" herein in the context of treatment of PV infection, it is meant that the administration of that amount to an individual PV infected host, either in a single dose or as part of a series, that is effective for treatment of PV infection. By the use of the term "immunologically effective amount" herein in the context of prevention of PV infection, it is meant that the administration of that amount to an individual host, either in a single dose or as part of a series, that is effective to delay, inhibit, treat or prevent PV infection or disease. The effective amount varies depending upon the health and physical condition of the individual to be treated, the taxonomic group of individual to be treated, the capacity of the individual's immune system to synthesise antibodies, the degree of protection desired, the formulation of the immunogen, the assessment of the medical situation, and other relevant factors. It is expected that the amount will fall in a relatively broad range that can be determined through routine trials.

Preferably, the amino acid sequences in the polyprotein construct substantially correspond to the sequences of wild-type early ORF proteins of PV, including allelic or other variants thereof. Suitable variants include variants having single or multiple amino acid substitutions or additions to the wild-type sequences, and may have at least 50–60%, more preferably at least 70–80%, and most preferably at least 90%, similarity to the wild-type amino acid sequences, provided the variant is capable of eliciting an immune response against PV in a host animal. The amino acid sequences may also be immunogenic fragments of the wild-type early ORF proteins, that is fragments of the proteins which are capable of eliciting an immune response in a host animal. Suitably, the immunogenic fragment will comprise at least five, and more preferably at least ten, contiguous amino acid residues of the particular protein. Such immunogenic fragments may also be recognised by PV-specific antibodies, particularly antibodies which have a protective or therapeutic effect in relation to PV infection. Preferably, the immunogenic fragment is a non-full length fragment of a wild-type amino acid sequence, which may for example comprise a deletion mutant of an early ORF protein corresponding to at least 50%, more preferably 60–70%, and even 80–90% of the full length wild-type amino acid sequence.

The amino acid sequences in the polyprotein construct of the present invention may be selected from the group consisting of the E1, E2, E3, E4, E5 (E5a, E5b), E6, E7 and E8 proteins of PV, and may be included in the construct in any desired order. By way of example, the construct may be selected from the group consisting of:

(a) E6/E4
(b) E6/E5a/E4
(c) E6/E 7/E4
(d) E6/E7/E5a/E4
(e) E6/E7/E1/E4
(f) E6/E7/E5a/E1/E4
(g) E6/E7/E5a/E1/E2/E4
(h) E6/E7/E5a/E5b/E1/E2/E4
(i) E2/E5b
(j) E2/E1/E5b
(k) E2/E5a/E5b
(l) E2/E1/E5a/E5b
(m) E2/E4/E5a/E5b/E6/E7/E1
(n) E2/E3/E4/E5/E8/E6/E7/E1.

As described above, at least one of the early ORF proteins is other than the E6 or E7 proteins. Preferably one of the early ORF proteins in the construct is the E4 protein.

The polyprotein constructs of this invention preferably comprise at least three, and more preferably three, four or five early ORF protein sequences. In addition, two or more different polyprotein constructs based on different combinations of early ORF proteins and/or different PV genotypes may be included in a single composition for prophylactic or therapeutic use.

In the polyprotein constructs of this invention, the amino acid sequences may be fused or linked directly together. Alternatively, they may be linked with a linker sequence of from 1 to 50, preferably 1 to 20, and more preferably 1 to 5, amino acid residues between the separate amino acid sequences. By way of example, such a linker sequence may be an amino acid sequence encoded by the nucleotide sequence comprising a restriction endonuclease site. Linker sequences as described above may also be provided before and/or after the amino acid sequences in the polyprotein constructs.

The polyprotein constructs of this invention may also comprise a tag protein or peptide moiety fused or otherwise coupled thereto to assist in purification of the polyprotein construct. Suitable tag moieties include, for example, (His)$_6$, glutathione-S-transferase (GST) and FLAG (International Biotechnologies), with the (His)$_6$ tag moiety being preferred. The constructs may further comprise a component to enhance the immunogenicity of the polyprotein. The component may be an adjuvant such as diphtheria or cholera toxin or *E. coli* heat labile toxin (LT), or a non-toxic derivative thereof such as the holotoxoid or B subunit of cholera toxin or LT. In addition, the polyprotein construct of the invention may comprise a lipid binding region to facilitate incorporation into ISCOMs. Suitable lipid binding regions are disclosed by way of example in Australian Provisional Patent Application No. PN8867/96, dated Mar. 25, 1996. A preferred lipid binding region is an influenza haemagglutinin tail.

The present invention also provides a nucleic acid molecule comprising a sequence of nucleotides which encodes a polyprotein construct as broadly described above.

The nucleic acid molecule may be RNA or DNA, single stranded or double stranded, in linear or covalently closed circular form. It will be appreciated that the sequence of nucleotides of this aspect of the invention may be obtained from natural, synthetic or semi-synthetic sources; furthermore, this nucleotide sequence may be a naturally-occurring sequence, or it may be related by mutation, including single or multiple base substitutions, deletions, insertions and inversions, to such a naturally-occurring sequence, provided always that the nucleic acid molecule comprising such a sequence is capable of being expressed as a polyprotein construct as described herein.

The nucleotide sequence may have expression control sequences positioned adjacent to it, such control sequences being derived from either a homologous or a heterologous source.

Since nucleic acid molecules may be delivered directly as "naked DNA" to a host animal, (see, for example, Wolfe et al., 1990, *Science* 247:1465 and Fynan er al., 1993, *Proc. Natl. Acad. Sci.* USA, 90:11478), the present invention also includes a nucleic acid vaccine composition comprising a nucleic acid molecule as described above, together with a pharmaceutically acceptable carrier and/or diluent.

Immunisation with an isolated nucleic acid molecule allows in vivo synthesis of the encoded polyprotein construct by the host animal in a manner similar to the manner in which PV proteins are expressed during infection by PV. In this aspect, the present invention also extends to a method for eliciting an immune response against PV in a host animal, which method comprises administering to the host animal an immunologically effective amount of a nucleic acid molecule as described above. The invention also extends to use of such a nucleic acid molecule in eliciting an immune response against PV in a host animal.

This invention also provides a recombinant DNA molecule comprising an expression control sequence having promoter and initiator sequences, the nucleotide sequence encoding the polyprotein construct being located 3' to the promoter and initiator sequences and a terminator sequence located 3' to this sequence of nucleotides. In yet another aspect, the invention provides a recombinant DNA cloning vehicle such as a plasmid capable of expressing the polyprotein construct, as well as a host cell containing a recombinant DNA cloning vehicle and/or a recombinant DNA molecule as described above.

Suitable expression control sequences and host cell/cloning vehicle combinations are well known in the art, and are described by way of example, in Sambrook et al. (1989) Molecular Cloning: A Laboratory Manual, 2nd ed. Cold Spring Harbor, N.Y., Cold Spring Harbor Laboratory Press. Thus, the nucleotide sequence may be ligated into any suitable expression vector, which may be either a prokaryotic or eukaryotic expression vector. Preferably, the vector is a prokaryotic expression vector such as pTrcHisA or pGEX-STOP (a pGEX expression vector (Amrad/Pharmacia Biotech) which has been manipulated so as to result in truncation of the GST moiety, disclosed in Australian Provisional Patent Application No. PN8272/86, dated Feb. 26, 1996). Whilst the host cell is preferably a prokaryotic cell, more preferably a bacterium such as *E. coli.*, it will be understood that the host cell may alternatively be a yeast or other eukaryotic cell, or insect cells infected with baculovirus or the like.

Once recombinant DNA cloning vehicles and/or host cells expressing a polyprotein construct of this invention have been identified, the expressed polypeptides synthesised by the host cells, for example, as a fusion protein, can be isolated substantially free of contaminating host cell components by techniques well known to those skilled in the art.

The polyprotein construct-encoding DNA sequence is formed by linking or "fusing" sequences encoding each of the individual protein moieties. The first sequence in the polyprotein DNA construction has a promoter element and a ribosome binding site. These elements assure that transcription of the polyprotein DNA into mRNA begins at a defined site and that the signal, the ribosome binding site, needed for translation of mRNA into protein is present. Synthesis of the polyprotein is made continuous from one protein component to the next by removing or altering any initiation or binding signals and stop codons from the subsequent proteincoding sequences. The stop codon, normally a signal for the ribosome to stop translation and to end the polypeptide, is not altered or removed from the last DNA sequence. The individual protein encoding sequences are jointed such that a proper phasing is made of the mRNA reading frames for translation of the sequence into the desired amino acids. Once a DNA sequence encoding a polyprotein construct or a "polyprotein gene" is made, it is necessary to demonstrate that the construction leads to production of a stable polyprotein construct. If the resulting protein is not stable, for example because the junctions between the proteins are vulnerable to proteolytic digestion, then the junction regions are modified. This can be done by inserting different amino acids at or near the junction or by building spacers of amino acids between the individual proteins. Linkers or spacers can also be introduced to modify the overall activity of the polyprotein. By adjusting the space between and orientation of the individual proteins it is possible to modify the total activity of the polyprotein construct. Further details of the preparation of polyprotein constructs of the present invention by recombinant DNA techniques are disclosed, by way of example, in U.S. Pat. No. 4,774,180, the disclosure of which is incorporated herein by reference.

Preferably, the polymerase chain reaction (PCR) is used to amplify the nucleotide sequences encoding each of the individual PV early ORF proteins. The nucleotide sequences which are amplified may be full length or non full-length fragments thereof. Restriction endonuclease sites may be incorporated in the oligonucleotide primers used for PCR to furnish directional ligation of the amplification products in the same translational frame and to enable directional cloning into a suitable expression vector. The primers may encode an artificial initiator codon or a termination codon.

The first nucleotide sequence has an initiator codon. This initiator codon may either be the normal wild-type initiator codon of the first sequence or may be inserted artificially at another chosen position of this sequence. Synthesis of the polyprotein construct is made continuous from one protein component to the next by removing or altering any initiation or binding signals and termination codons. The termination codon must be present in the last nucleotide sequence. This is effected normally by not altering or removing the termination codon of the last nucleotide sequence. However, this termination codon may be inserted artificially, by methods known to persons skilled in the art, by first removing the normal, wild-type termination codon of the last nucleotide sequence and inserting another, in the correct reading frame, at another position of this sequence.

The polyprotein construct-encoding DNA sequence may incorporate restriction sites at the flanking ends to facilitate insertion of the DNA sequence into a suitable expression vector.

The PV can be a human or an animal PV, and is preferably HPV. The HPV may be of any genotype, and may for example be selected from the group consisting of HPV-6, HPV-11, HPV-16, HPV-18, HPV-33, HPV-35, HPV-31 and HPV45. Preferably, the HPV is HPV-6 or HPV-11.

The present invention is particularly, but not exclusively, directed to polyprotein constructs comprising early ORF proteins of the HPV-6 and HPV-11 genotypes which are causative agents of condylomata acuminata, however it will be appreciated that the invention extends to variants of the corresponding proteins in other HPV genotypes, particularly the HPV-16 and HPV-18 genotypes, and other genotypes which have oncogenic potential of a type similarto HPV-16 and HPV-18.

The polyprotein constructs of the present invention may comprise early ORF proteins of a single HPV genotype, or alternatively they may comprise early ORF proteins from more than one HPV genotype. In addition, a combination of more than one polyprotein construct may be used in cases where not all early ORF proteins are represented in the one polyprotein construct, or where immune responses to more than one HPV genotype are desired.

The polyprotein constructs of the present invention are provided as isolated proteins, that is they are substantially free of other PV proteins, and find particular utility for the treatment of genital warts, cervical cancer or other conditions caused by HPV in man. The polyprotein constructs can be included in pharmaceutical compositions for the treatment or prevention of diseases involving HPV as well as the other conditions discussed above.

The polyprotein constructs of the invention may be used to raise antibodies and/or induce cellular immune responses, either in subjects for which protection against infection by PV is desired, i.e. as prophylactic vaccines, or to heighten the immune response to an PV infection already present, i.e. as therapeutic vaccines. They also can be injected into production species to obtain antisera. In lieu of the polyclonal antisera obtained in the production species, monoclonal antibodies may be produced using the standard methods or by more recent modifications thereof by immortalising spleen or other antibody-producing cells for injection into animals to obtain antibody-producing clones. The polyclonal or monoclonal antibodies obtained, corrected if necessary for species variations, can also be used as therapeutic agents.

Direct administration of the polyprotein constructs to a host animal such as a human can confer either protective immunity against PV or, if the subject is already infected, a boost to the subject's own immune response to more effectively combat the progress of the PV induced disease.

The magnitude of the prophylactic or therapeutic dose of a polyprotein constructs of this invention will, of course, vary with the group of patients (age, sex, etc.), the nature or the severity of the condition to be treated and with the particular polyprotein construct and its route of administration. In general, the weekly dose range for use lies within the range of from about 0.1 to about 5 µg per kg body weight of a mammal.

Any suitable route of administration may be employed for providing a mammal, especially a human, with an effective dosage of a polyprotein construct of this invention. For example, oral, rectal, vaginal, topical, parenteral, ocular, nasal, sublingual, buccal, intravenous and the like may be employed. Dosage forms include tablets, troches, dispersions, suspensions, solutions, capsules, creams, ointments, suppositories, aerosols and the like. Said dosage forms also include injected or implanted slow releasing devices specifically designed for this purpose or other forms of implants modified to additionally act in this fashion.

If the polyprotein constructs are to be administered as vaccines, they are formulated according to conventional methods for such administration to the subject to be protected. The polyprotein constructs may be delivered in accordance with this invention in ISCOMS™ (immune stimulating complexes), liposomes or encapsulated in compounds such as acrylates or poly(DL-lactide-co-glycoside) to form microspheres. They may also be incorporated into oily emulsions and delivered orally.

Other adjuvants, as well as conventional pharmaceutically acceptable carriers, excipients, buffers or diluents, may also be included in vaccine compositions of this invention. Generally, a vaccine composition in accordance with the present invention will comprise an immunologically effective amount of the polyprotein construct, and optionally an adjuvant, in conjunction with one or more conventional pharmaceutically acceptable carriers and/or diluents. An extensive though not exhaustive list of adjuvants can be found in Coulter and Cox, "Advances in Adjuvant Technology and Application", in *Animal Parasite Control Utilizing Biotechnology*, Chapter 4, Ed. Young, W. K., CRC Press, 1992. As used herein "pharmaceutically acceptable carriers and/or diluents" include any and all solvents, dispersion media, aqueous solutions, coatings, antibacterial and antifungal agents, isotonic and absorption delaying agents and the like. The use of such media and agents for pharmaceutical active substances is well known in the art and is described by way of example in *Remington's Pharmaceutical Sciences*, 18th Edition, Mack Publishing Company, Pennsylvania, U.S.A.

In practical use, a polyprotein construct of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous and intraarterial). In preparing the compositions for oral dosage form, any of the usual pharmaceutical media may be employed, such as, for example, water glycols, oils, alcohols, flavouring agents, preservatives, colouring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit torm, in which case solid pharmaceutical carriers are obviously employed. If desired, tablets may be sugar-coated or enteric-coated by standard techniques.

In addition to the common dosage forms set out above, the polyprotein constructs of this invention may also be administered by controlled release means and/or delivery devices, including by way of example, the controlled release preparations disclosed in International Patent Specification No. PCT/AU93/00677 (Publication No. WO 94115636).

Pharmaceutical compositions of the present invention suitable for oral or parenteral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

Further features of the present invention are more fully described in the following Example(s). It is to be understood, however, that this detailed description is included solely for the purposes of exemplifying the present invention, and should not be understood in any way as a restriction on the broad description of the invention as set out above.

EXAMPLES

Example 1

Amplification and Cloning of Early Open Reading Frames (ORFS) of HPV6b

A clone containing the entire genome of HPV6b in pBR322 (de Villiers, 1981, *J. Virol*, 40:932) was used as the template for separate PCR amplifications of E6, E7, E5a, E5b, E1, E2 and E4 open reading frame (ORF) sequences.

Appropriate restriction enzyme recognition sequences were included in the oligonucleotides used for amplification (Table I; 1–7) to allow sequential assembly of these amplified early gene sequences into a "polyprotein" sequence as depicted in FIG. 1A.

In this scheme, E6 was amplified with oligonucleotides containing a SmaI site at the 5' end and HindIII, NcoI and XbaI sites at the 3' end. As well, E4 was amplified with oligonucleotides containing XbaI, SacI, KpnI and SpeI sites 5' and a Bg/II site 3'.

These amplified fragments were cloned as SmaI/XbaI (E6) and XbaI/Bg/II (E4) FIG. 1B) in the vector pSP70 (Promega Corporation) which had been modified by the removal of an EcoRV/EcoRI fragment to contain a portion of the pGEM3Zf (Promega Corporation) polylinker—HinduI through EcoRI. As well, unwanted sites upstream of the SmaI site were removed by cleaving with SmaI/XhoI and insertion of a SmaI/Sa/l/XhoI linker to create the vector pSP70 (MOD).

The E6/E4 cassette was able to be removed by cleavage with SmaI/Bg/II and this was then cloned for expression into the pGEX-STOP vector which produces a non-fusion protein with a C-terminal six-histidine sequence for purification purposes.

Using the introduced restriction enzyme recognition sequences, other early ORF sequences were incorporated into the E6/E4 cassette cloned into pSP70 (MOD) and then the newly created cassette cloned as a SmaI/BgII fragment into pGEX-STOP.

In this manner polyprotein constructs containing E6/E5a/E4, E6/E7/E4, E6/E7/E5a/E4, E6/E7/E1/E4 and E6/E7/E5a/E1/E4 were assembled. Complete DNA sequence data for the first three constructs is included and sequence data across the junctions of E1 is included for the latter two. DNA sequencing revealed the SpeI site was inactivated by a single base change which occurred either during oligonucleotide synthesis, PCR or cloning.

As well the tetrafusion construct of E6/E7/E5a/E4 was cloned for expression into pET23b (Novagen) by firstly subcloning the tetramer as a SmaI/BgfII fragment into the SmaI/BamHI sites of the vector pRIT2T (AMRAD Pharmacia Biotech). The tetramer was then removed by restriction with SmaI and Sa/I and cloned into the HincII/XhoI sites of the vector pET23b.

A further construct containing E2 and E5b, but which could also accommodate the addition of E1 and E5a, was created by amplifying E2 with oligonucleotides containing a SmaI site at the 5' end and XbaI, NcoI, KpnI and SadcI, sites at the 3' end (Table 1; 8) and with E5b amplified using oligonucleotides with an XbaI site 5' and XhoI, BglII sites 3' (Table 1; 9). These amplified fragments were then cloned into pSP70 (MOD) as depicted in FIG. 1C.

TABLE 1

| | Oligonucleotides used for PCR | |
|---|---|---|
| Early gene | Forward | Reverse |
| 1 E6 | 5'GCGCCCCGGGATGGAAAGTGC AAATGCCTC3' (SEQ ID No. 1) | 5'GCGCTCTAGACCATGGAAGCT TGGGTAACATGTCTTCCATGC3' (SEQ ID. No.2) |
| 2 E4 | 5'GCGCTCTAGAGAGCTCGGTACC ACTAGTGGAGCACCAAACATTGG GAAG3' (SEQ ID No. 3) | 5'GCGCAGATCTTAGGCGTAGCT GAACTGTTAC3' (SEQ ID No. 4) |
| 3 E5a | 5'GCGCCCATGGGAAGTGGTGCCT GTACAAATAGC3' (SEQ ID No. 5) | 5'GCGCTCTAGATTGCTGTGTGG TAACAATATAG3' (SEQ ID No. 6) |
| 4 E7 | 5'GCGCAAGCTTCATGGAAGACAT GTTACCCTAAAG3' (SEQ ID No. 7) | 5'GCGCCCATGGGGTCTTCGGT GCGCAGATGG3' (SEQ ID No. 8) |
| 5 E1 | 5'GCGCGAGCTCGCGGACGATTCA GGTACAGAAAATG3' (SEQ ID No. 9) | 5'GCGCGGTACCTAAAGTTCTAA CAACTGTTCCTG3' (SEQ ID No. 10) |

TABLE 1-continued

Oligonucleotides used for PCR

| Early gene | Forward | Reverse |
|---|---|---|
| 6 E2 | 5'GCGCGGTACCGAAGCAATAGCC AAGCGTTTAG3' (SEQ ID No. 11) | 5'GCGCACTAGTCAATAGGTGCA GTGACATAAATC3' (SEQ ID No. 12) |
| 7 E5b | 5'GCGCTCTAGACTAACATGTCAAT TTAATGATG3' (SEQ ID No. 13) | 5'GCGCGAGCTCATTCATATATA TATAATCACC3' (SEQ ID No. 14) |
| 8 E2 | 5'GCGCCCCGGGATGGAAGCAATA GCCAAGCG3' (SEQ ID No. 15) | 5'GCGCTCTAGACCATGGGGTAC CGAGCTCCAATAGGTGCAGTG ACATAAATC3' (SEQ ID No. 16) |
| 9 E5 b | 5'GCGCTCTAGACTAACATGTCAAT TTAATGATG3' (SEQ ID No. 17) | 5'GCGCAGATCTCTCGAGATTCA TATATATAATCAC3' (SEQ ID No. 18) |

Example 2

Expression of Different Polyprotein Constructs

The following constructs in pGEX-STOP were expressed in E. coli strain BL21 and protein production was assayed by PAGE followed by Western blotting:

i) E6/E4
ii) E6/E5a/E4
iii) E6/E7/E4
iv) E6/E7/E5a/E4

Construct (iv) in pET23b, expressed in E. coli strains BL21(DE3)pLysS and D494(DE3)pLysS (Novagen), was also assayed for protein production by Western blotting and also by Coomassie Blue staining for the latter strain.

Cultures of 200 mL were grown in Terrific broth (Tartoff and Hobbs, Focus, 9:12, 1987) in the presence of 100 µg/mL ampicillin (BL21) and 34 µg/ml cloramphenicol [BL21 (DE3)pLysS] and 15 µg/mL kanamycin [AD494(DE3) pLysS]. At $OD_{600}$~1 protein expression was induced by the addition of IPTG to 0.4 mM. Following induction samples were taken at 1, 2, 3, 4 and 5 hours and in some cases after overnight culture.

Figure 2:
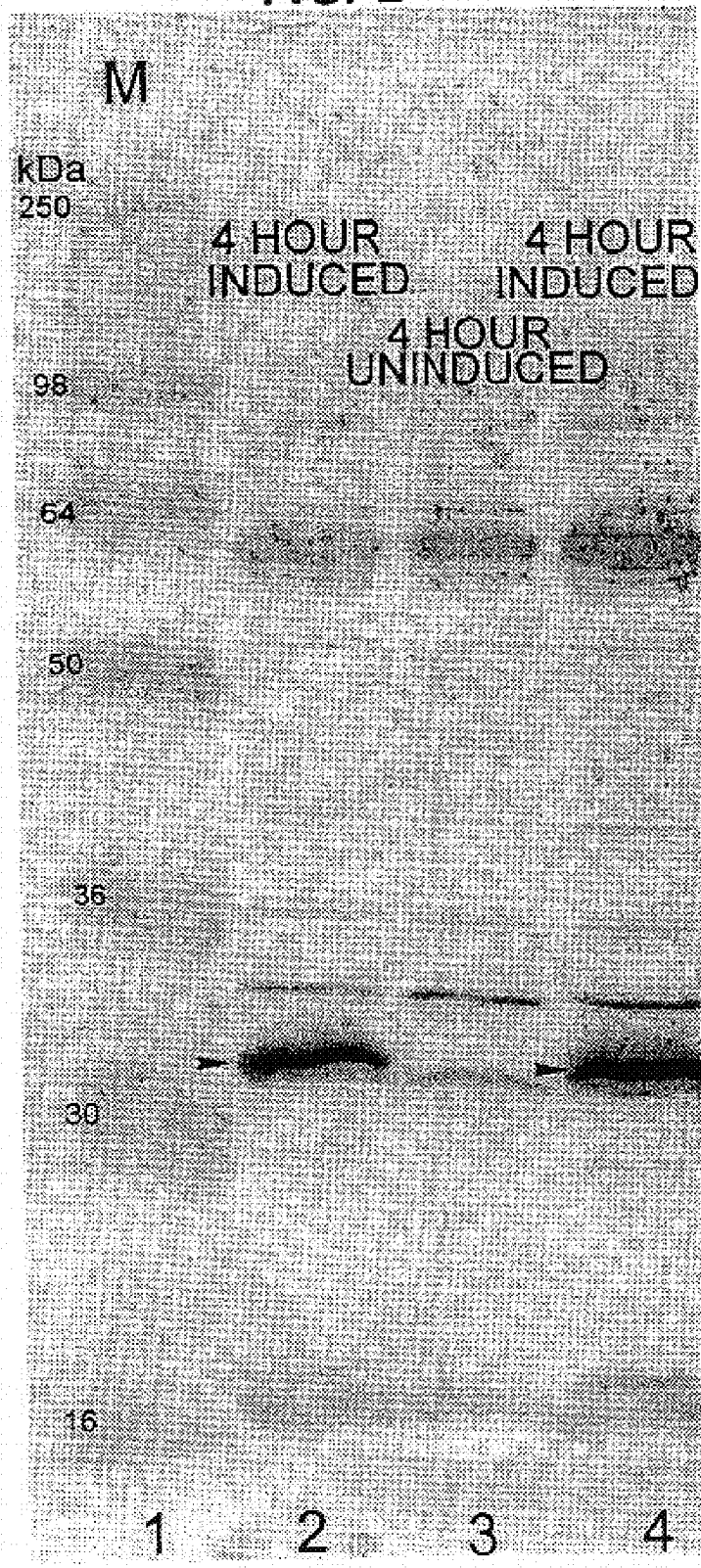

FIG. 2 show a Western blot result for the E6/E4 construct. This was probed with a polyclonal rabbit anti E4 antibody (MWE4—raised to the peptide LGNEHEESNSPLAT-PCVWPT conjugated to ovalbumin). An immunoreactive band of ~30 kDa was present in the 4—hour-induced sample (lanes 2 & 4, arrow) which was not present in the uninduced sample (lane 3).

Figure 3:
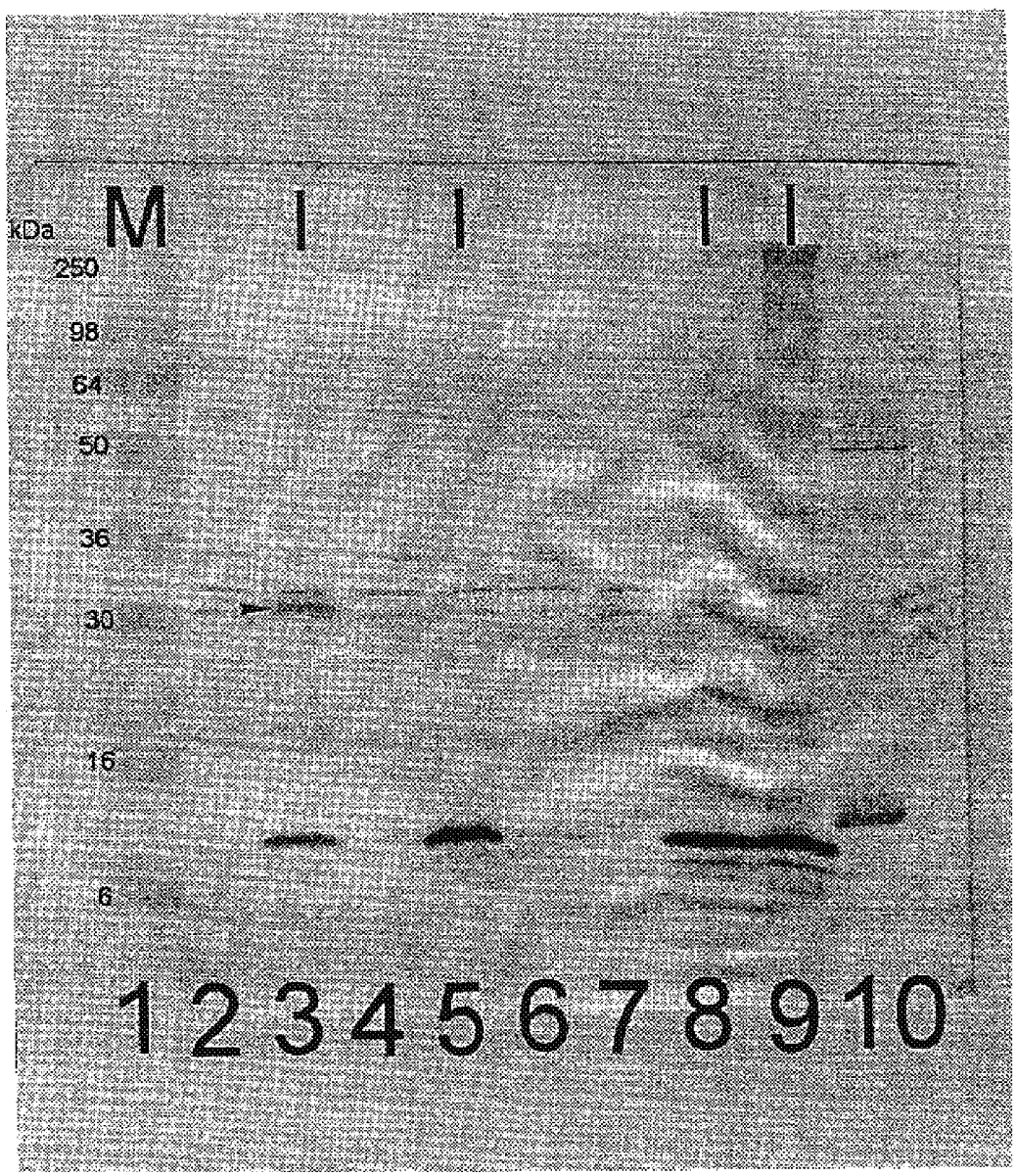

The same ~30 kDa band can also be seen in the induced sample in FIG. 3, lane 3, arrow (lane 2-uninduced) while the E6/E5a/E4 trimer construct of ~40kDa was poorly represented after a 4 hour induction period (lane 5, arrow; uninduced sample-lane 4) using the same anti-E4 antibody.

Figure 4:
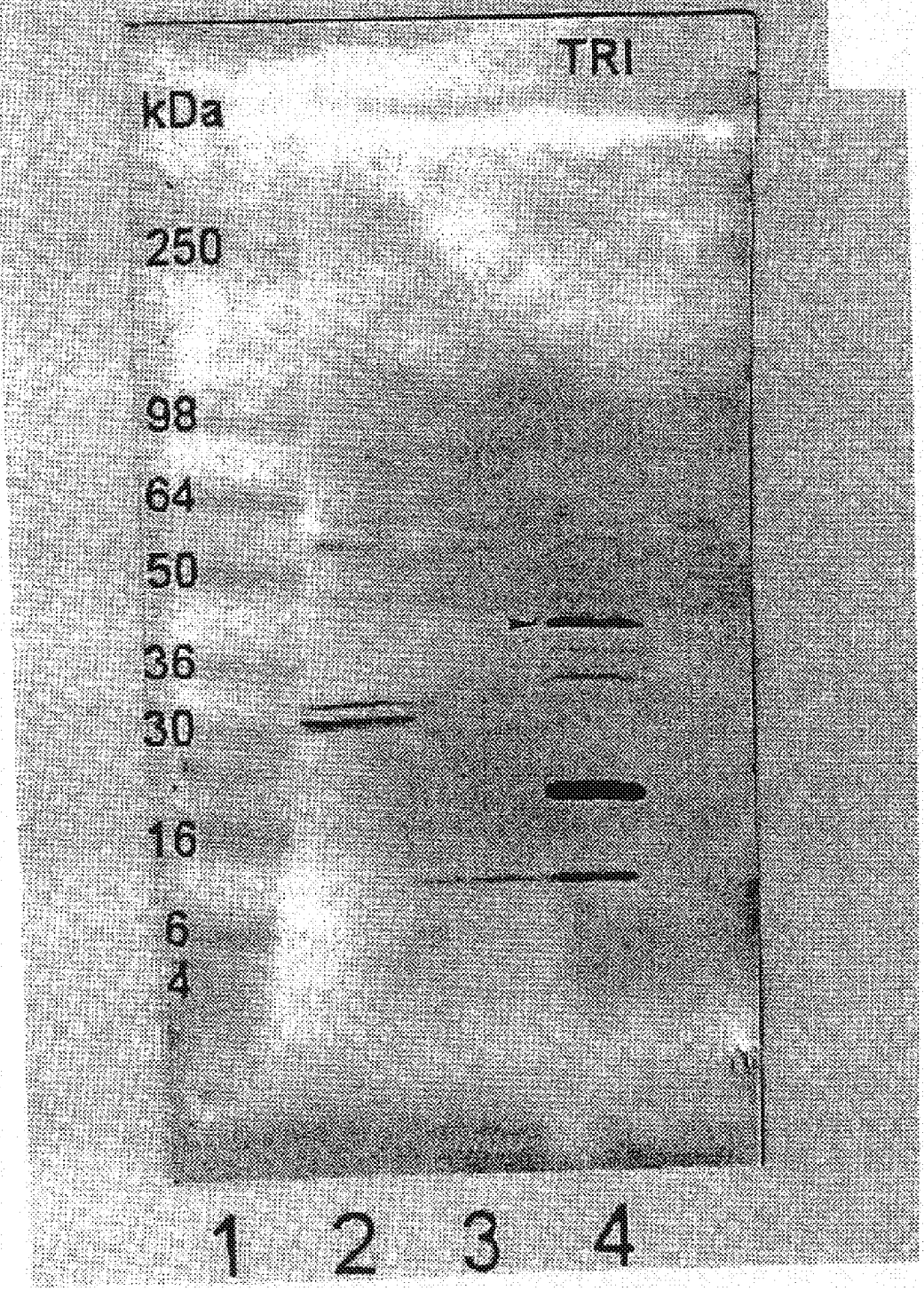

In contrast however, a trimer construct of E6/E7/E4 (~41 kDa) could be easily detected after 5 hours induction using an anti-hexahistidine monoclonal antibody (Dianova) [FIG. 4, lane 4, arrow; uninduced sample—lane 3].

Figure 5:
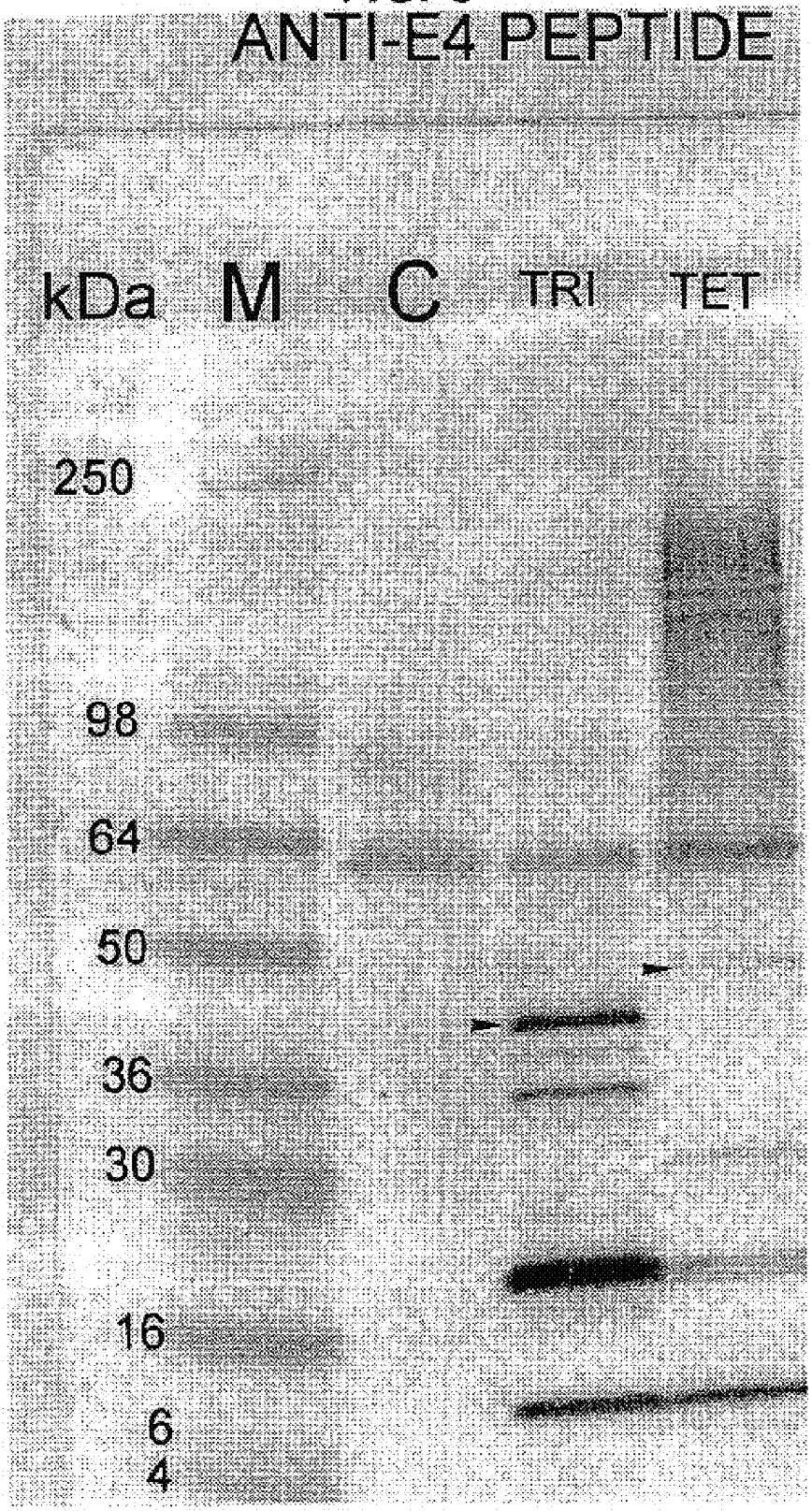

The same trimer construct was again easily visualised after 5 hours induction using the anti-E4 antibody MWE4 (FIG. 5, lane TRI, arrow; control sample—lane C) and the tetramer consisting of E6/E7/E5a/E4 (~51 kDa) could also be detected (lane TET, arrow). Although this band is weak, it must be noted that a considerable amount of high molecular weight material is also immunoreactive, indicating the tetramer is reasonably well expressed but possibly prone to aggregation.

Figure 6:
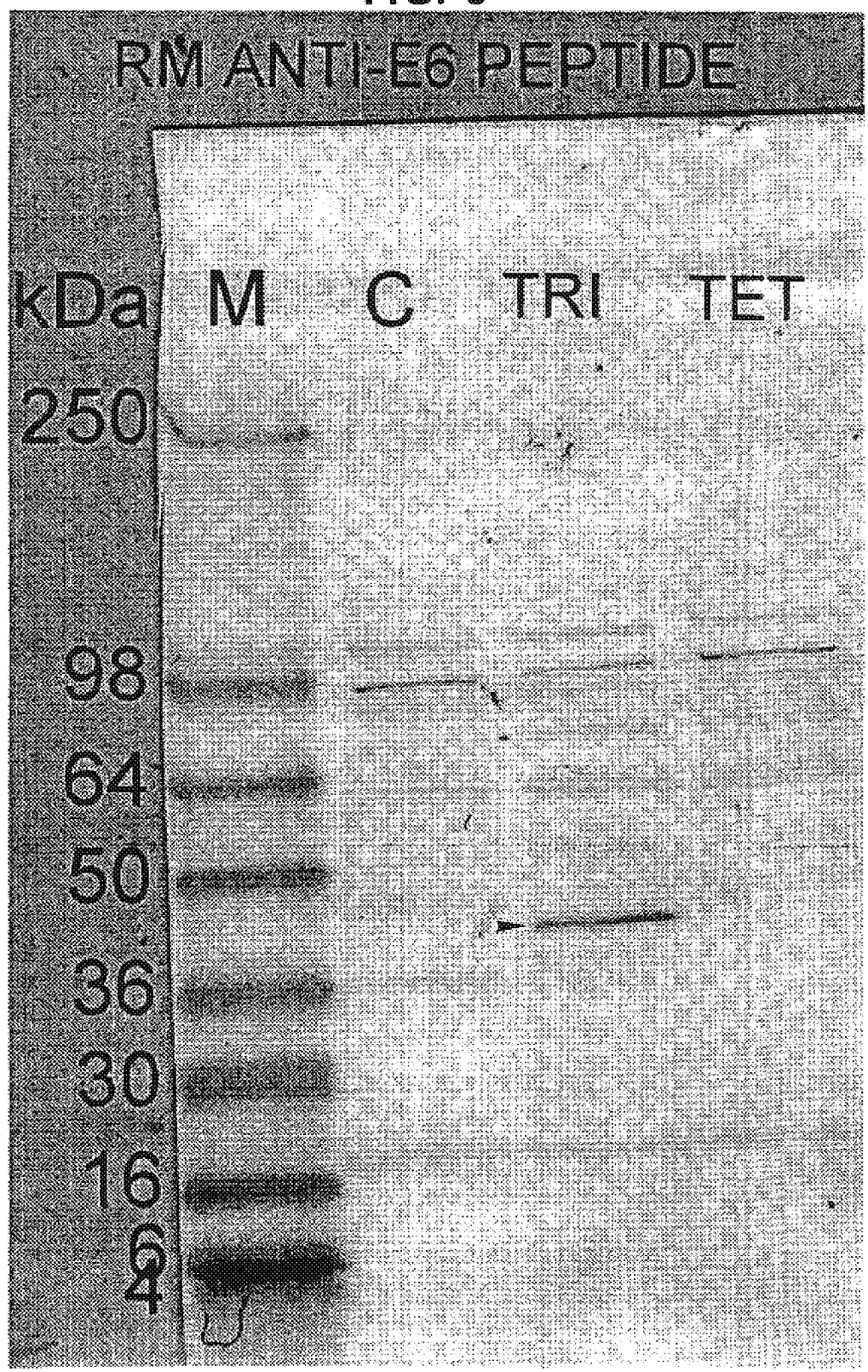
Figure 7:
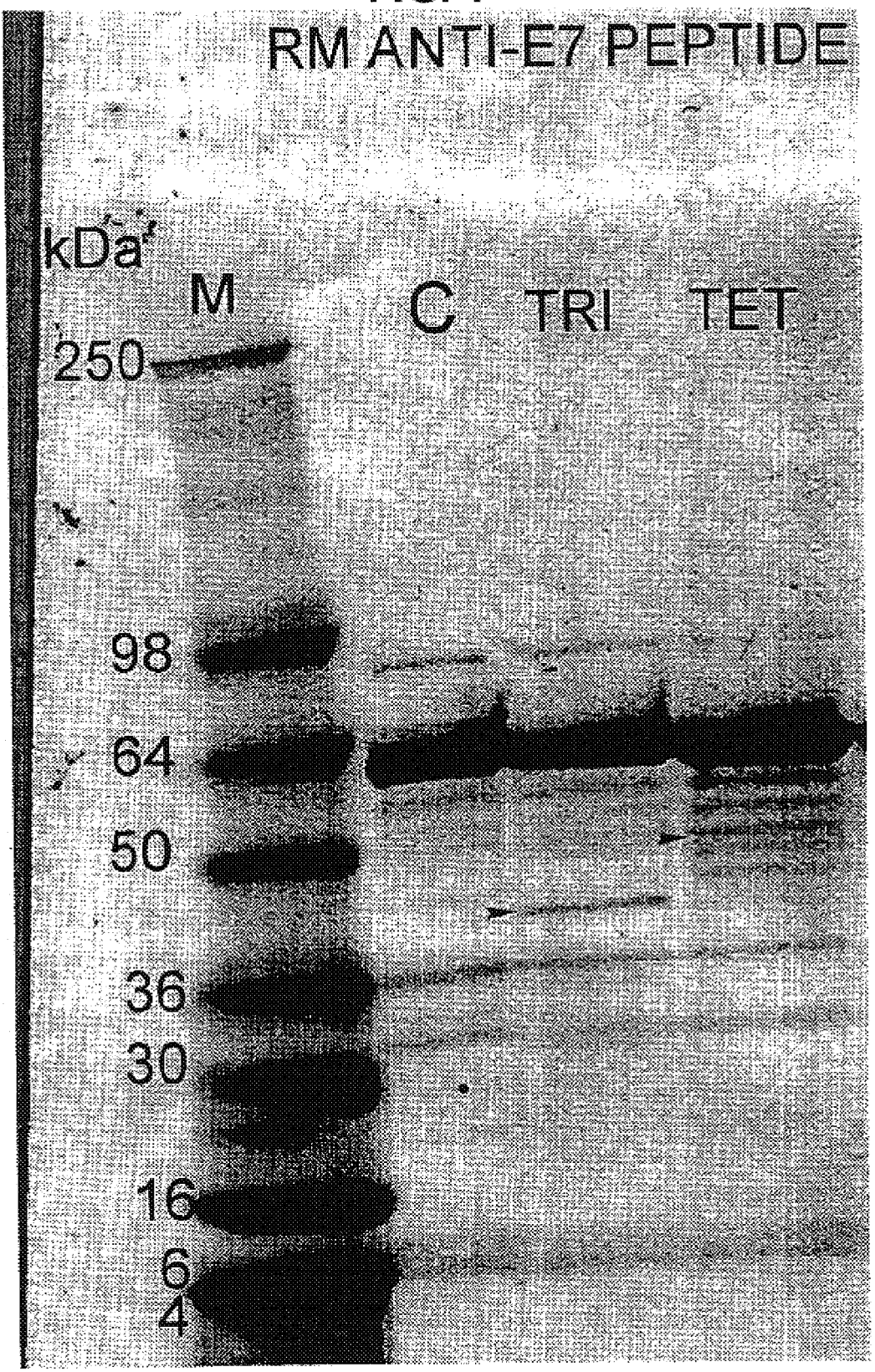

FIG. 6 indicates that an anti-E6 antibody (prepared as described below) was able to detect E6/E7/E4 after 5 hours induction (lane TRI, arrow) but not E6/E7/E5a/E4 (lane TET; lane C—uninduced). However, an anti-E7 antibody (prepared as described below) was able to detect after 5 hours induction both the trimer (FIG. 7, lane TRI, arrow; lane C—uninduced) and the tetramer (lane TET, arrow; lane C—uninduced), with the latter again showing indications of aggregation. A monoclonal antibody raised to an E4 peptide also recognised the trimer.

Figure 8:
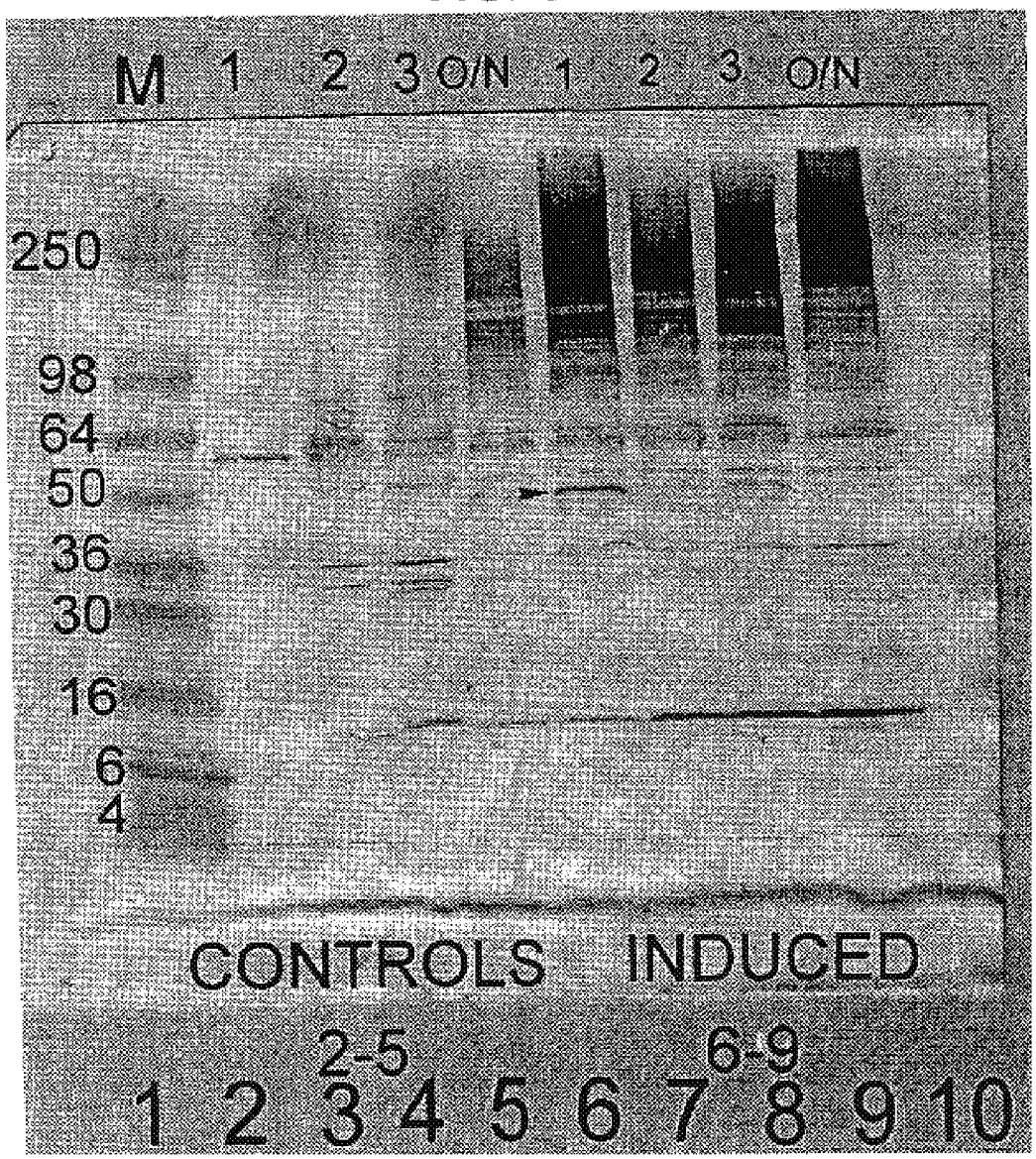
Figure 9:
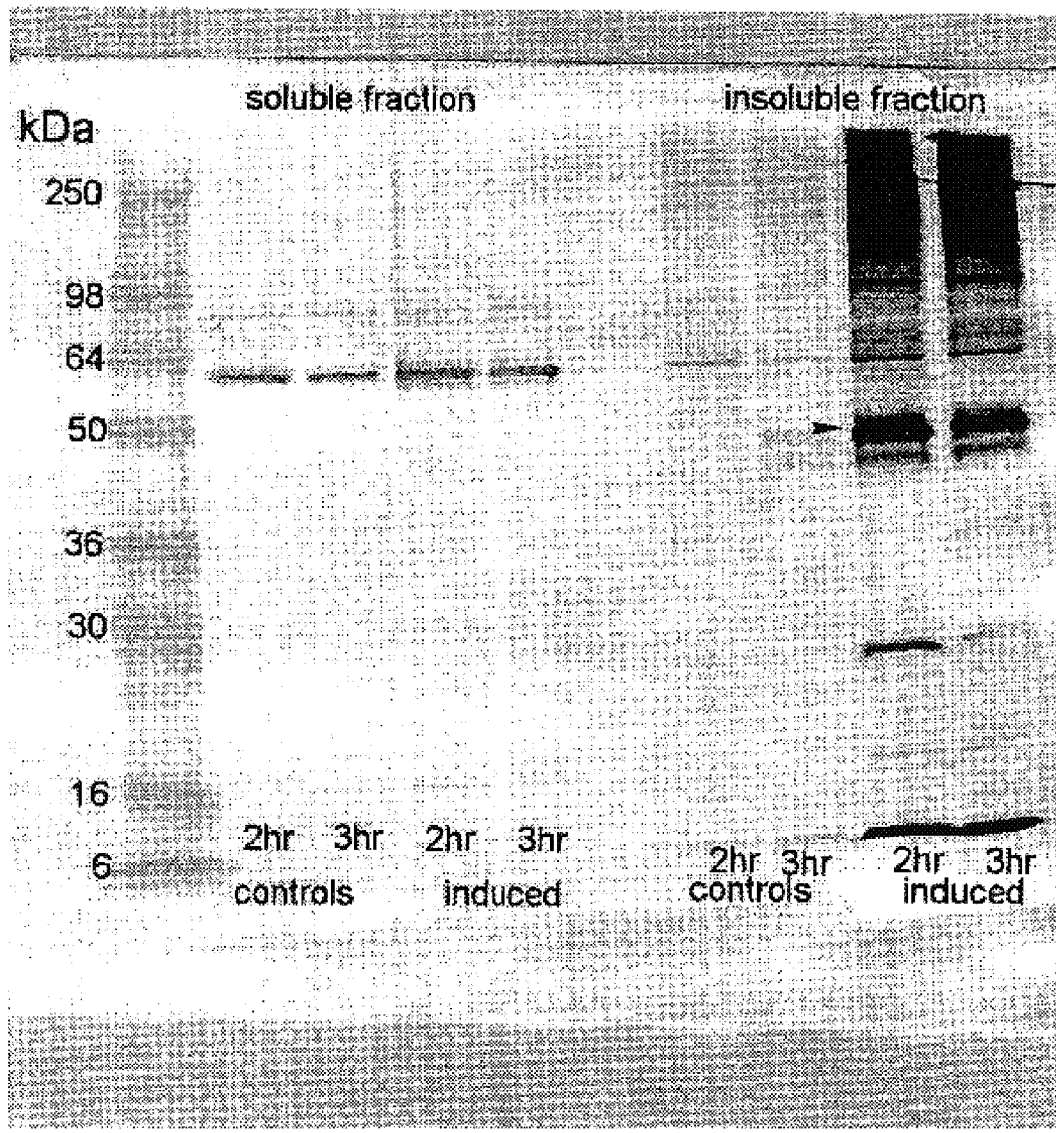

The phenomenon of aggregation was clearly apparent when the E6/E7/E5a/E4 tetramer was expressed in the pET23b plasmid in BL21 (DE3)pLysS (FIG. 8—a Western blot probed with MWE4). Lanes 2–5 are 1 hour, 2 hour, 3 hour and overnight uninduced samples and lanes 69 represent 1 hour, 2 hour, 3 hour and overnight induced samples. After 1 hour induction a band of E6/E7/E5a/E4 can clearly be seen (arrow), but with increased times of induction this seems to decrease and aggregated forms are increased. In contrast, when strain AD494(DE3)pLysS was used to express the tetramer, a substantial signal was obtained at the~50 kDa position on a Western blot of the insoluble fraction (FIG. 9, arrow) following 2 hours induction, which still persisted at 3 hours. This immunoreactive band was not present in control samples and no protein was detected in the samples from the soluble fractions.

Figure 10:
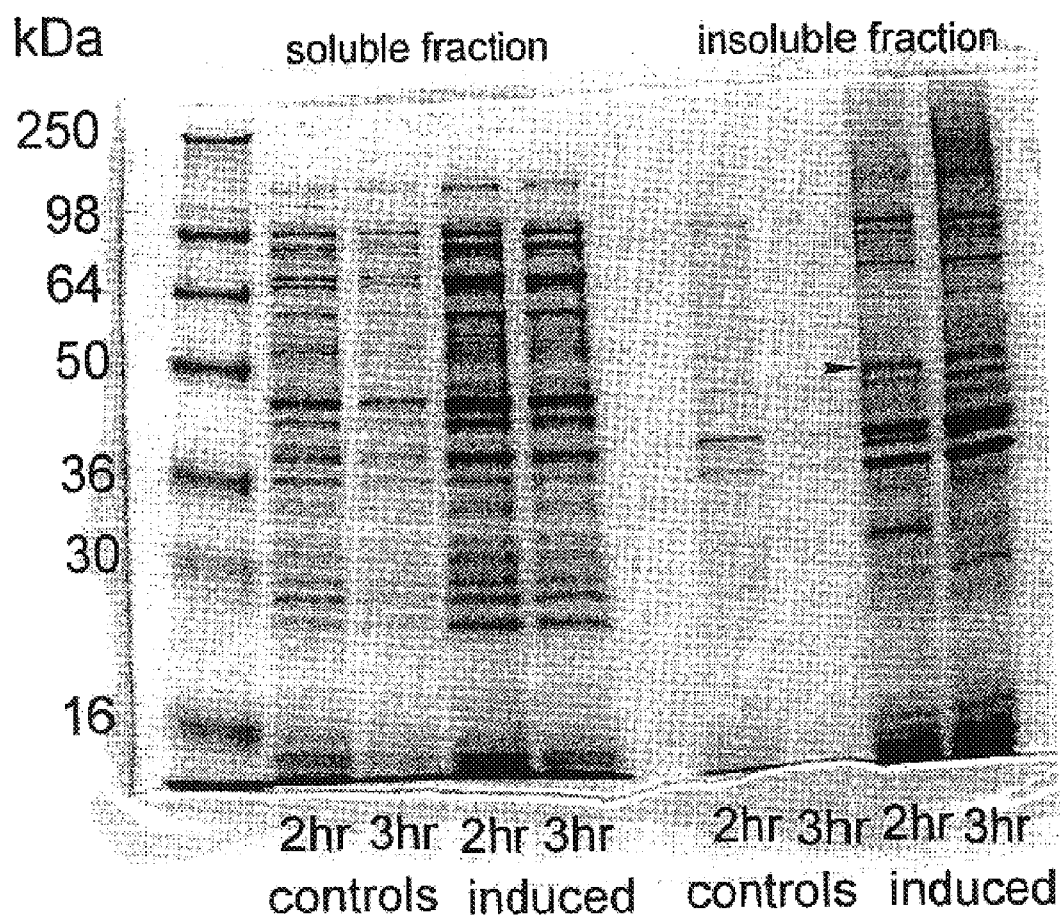

FIG. 10 shows the Coomassie stained profile of an identical gel, indicating that the immunoreactive bands present after 2 and 3 hours induction (FIG. 9) can clearly be visualised as stained bands (arrow) which are not present in the control samples.

Example 3

DNA Sequencing of Polyprotein Constructs

Polyprotein constructs were sequenced in both directions by the dideoxy method using primers that generated overlapping sequence information. The $^{77}$Sequencing™ Kit (Pharmacia was used to generate $^{35}$S-labelled chain-terminated fragments which were analysed on a Sequi-Gen™ (Biorad) electrophoretic gel apparatus. The DNA and corresponding amino acid sequences for E6/E5a/E4 (CSL690.SEQ), E6/E7/E4 (CSL760.SEQ) and E6/E7/E5a/E4 (CSL673.SEQ) are shown below. (SEQ ID Nos: 19 and 20, 21 and 22, and 23 and 24, respectively).

For constructs E6/E7/E1/E4 (CSL 791) and E6/E7/E5a/E1/E4 (CSL 762), which created from E6/E7/E4 and E6/E7/E5a/E4, respectively, DNA sequence analysis across the junctions of E1 with its neighbours is shown below (SEQ ID Nos. 25 and 26, 27 and 28, and 29 and 30, respectively).

```
File: CSL690.SEQ
Range: 1-11 Mode: Normal
Codon Table: Universal
         E6/E5a/E4 - SEQ ID Nos, 19 (DNA) and 20 (amino acid)

9          18          27          36          45          54
5' ATG GAA AGT GCA AAT GCC TCC ACG TCT GCA ACG ACC ATA GAC CAG TTG TGC AAG
   --- --- --- --- --- --- --- --- --- --- --- --- --- --- --- --- --- ---
   Met Glu Ser Ala Asn Ala Ser Thr Ser Ala Thr Thr Ile Asp Gln Leu Cys Lys
             63          72          81          90          99         108
   ACG TTT AAT CTA TCT ATG CAT ACG TTG CAA ATT AAT TGT GTG TTT TGC AAG AAT
   --- --- --- --- --- --- --- --- --- --- --- --- --- --- --- --- --- ---
   Thr Phe Asn Leu Ser Met His Thr Leu Gln Ile Asn Cys Val Phe Cys Lys Asn
            117         126         135         144         153         162
   GCA CTG ACC ACA GCA GAG ATT TAT TCA TAT GCA TAT AAA CAC CTA AAG GTC CTG
   --- --- --- --- --- --- --- --- --- --- --- --- --- --- --- --- --- ---
   Ala Leu Thr Thr Ala Glu Ile Tyr Ser Tyr Ala Tyr Lys His Leu Lys Val Leu
            171         180         189         198         207         216
   TTT CGA GGC GGT TAT CCA TAT GCA GCC TGC GCG TGC TGC CTA GAA TTT CAT GGA
   --- --- --- --- --- --- --- --- --- --- --- --- --- --- --- --- --- ---
   Phe Arg Gly Gly Tyr Pro Tyr ALa Ala Cys Ala Cys Cys Leu Glu Phe His Gly
            225         234         243         252         261         270
   AAA ATA AAC CAA TAT AGA CAC TTT GAT TAT GCT GGA TAT GCA ACA ACA GTT GAA
   --- --- --- --- --- --- --- --- --- --- --- --- --- --- --- --- --- ---
   Lys Ile Asn Gln Tyr Arg His Phe Asp Tyr Ala Gly Tyr Ala Thr Thr Val Glu
            279         288         297         306         315         324
   GAA GAA ACT AAA CAA GAC ATC TTA GAC GTG CTA ATT CGG TGC TAC CTG TGT CAC
   --- --- --- --- --- --- --- --- --- --- --- --- --- --- --- --- --- ---
   Glu Glu Thr Lys Gln Asp Ile Leu Asp Val Leu Ile Arg Cys Tyr Leu Cys His
            333         342         351         360         369         378
   AAA CCG CTG TGT GAA GTA GAA AAG GTA AAA CAT ATA CTA ACC AAG GCG CGG TTC
   --- --- --- --- --- --- --- --- --- --- --- --- --- --- --- --- --- ---
   Lys Pro Leu Cys Glu Val Glu Lys Val Lys His Ile Leu Thr Lys Ala Arg Phe
            387         396         405         414         423         432
   ATA AAG CTA AAT TGT ACG TGG AAG GGT CGC TGC CTA CAC TGC TGG ACA ACA TGC
   --- --- --- --- --- --- --- --- --- --- --- --- --- --- --- --- --- ---
   Ile Lys Leu Asn Cys Thr Trp Lys Gly Arg Cys Leu His Cys Trp Thr Thr Cys
            441         450         459         468         477         486
   ATG GAA GAC ATG TTA CCC AAG CTT CCA TGG GAA GTG GTG CCT GTA CAA ATA GCT
   --- --- --- --- --- --- --- --- --- --- --- --- --- --- --- --- --- ---
   Met Glu Asp Met Leu Pro Lys Leu Pro Trp Glu Val Val Pro Val Gln Ile Ala
            495         504         513         522         531         540
   GCA GGA ACA ACC AGC ACA TTC ATA CTG CCT GTT ATA ATT GCA TTT GTT GTA TGT
   --- --- --- --- --- --- --- --- --- --- --- --- --- --- --- --- --- ---
   Ala Gly Thr Thr Ser Thr Phe Ile Leu Pro Val Ile Ile Ala Phe Val Val Cys
            549         558         567         576         585         594
   TTT GTT AGC ATC ATA CTT ATT GTA TGG ATA TCT GAG TTT ATT GTG TAC ACA TCT
   --- --- --- --- --- --- --- --- --- --- --- --- --- --- --- --- --- ---
   Phe Val Ser Ile Ile Leu Ile Val Trp Ile Ser Giu Phe Ile Val Tyr Thr Ser
            603         612         621         630         639         648
   GTG CTA GTA CTA ACA CTG CTT TTA TAT TTA CTA TTG TGG CTG CTA TTA ACA ACC
   --- --- --- --- --- --- --- --- --- --- --- --- --- --- --- --- --- ---
   Val Leu Val Leu Thr Leu Leu Leu Tyr Leu Leu Leu Trp Leu Leu Leu Thr Thr
            657         666         675         684         693         702
   CCC TTG CAA TTT TTC CTA CTA ACT CTA CTT GTG TGT TAC TGT CCC GCA TTG TAT
   --- --- --- --- --- --- --- --- --- --- --- --- --- --- --- --- --- ---
   Pro Leu Gln Phe Phe Leu Leu Thr Leu Leu Val Cys Tyr Cys Pro Ala Leu Tyr
            711         720         729         738         747         756
   ATA CAC TAC TAT ATT GTT ACC ACA CAG CAA TCT AGA GAG CTC GGT ACC ACT AAT
   --- --- --- --- --- --- --- --- --- --- --- --- --- --- --- --- --- ---
   Ile His Tyr Tyr Ile Val Thr Thr Gln Gln Ser Arg Glu Leu Gly Thr Thr Asn
            765         774         783         792         801         810
   GGA GCA CCA AAC ATT GGG AAG TAT GTT ATG GCA GCA CAG TTA TAT GTT CTC CTG
   --- --- --- --- --- --- --- --- --- --- --- --- --- --- --- --- --- ---
   Gly Ala Pro Asn Ile Gly Lys Tyr Val Met Ala Ala Gln Leu Tyr Val Leu Leu
            819         828         837         846         855         864
   CAT CTG TAT CTA GCA CTA CAC AAG AAG TAT CCA TTC CTG AAT CTA CTA CAT ACA
   --- --- --- --- --- --- --- --- --- --- --- --- --- --- --- --- --- ---
   His Leu Tyr Leu Ala Leu His Lys Lys Tyr Pro Phe Leu Asn Leu Leu His Thr
            873         882         891         900         909         918
   CCC CCG CAC AGA CCT CCA CCC TTG TGT CCT CAA GCA CCA AGG AAG ACG CAG TGC
   --- --- --- --- --- --- --- --- --- --- --- --- --- --- --- --- --- ---
   Pro Pro His Arg Pro Pro Pro Leu Cys Pro Gln Ala Pro Arq Lys Thr Gln Cys
            927         936         945         954         963         972
   AAA CGC CGC CTA GGA AAC GAG CAC GAG GAG TCC AAC AGT CCC CTT GCA ACG CCT
   --- --- --- --- --- --- --- --- --- --- --- --- --- --- --- --- --- ---
```

```
                                                   Lys Arg Arg Leu Gly Asn Glu His Glu Glu Ser Asn Ser Pro Leu Ala Thr Pro
                                                           981             990             999            1008            1017            1026
            TGT GTG TGG CCC ACA TTG GAC CCG TGG ACA GTG GAA ACC ACA ACC TCA TCA CTA
            Cys Val Trp Pro Thr Leu Asp Pro Trp Thr Val Glu Thr Thr Thr Ser Ser Leu
                    1035            1044            1053            1062            1071            1080
            ACA ATC ACG ACC AGC ACC AAA GAC GGA ACA ACA GTA ACA GTT CAG CTA CGC CTA
            Thr Ile Thr Thr Ser Thr Lys Asp Gly Thr Thr Val Thr Val Gln Leu Arg Leu
                    1089            1098            1107
            AGA TCT CAT CAC CAT CAC CAT CAC TAA 3'
            Arg Ser His His His His His His ***
File: CSL760.SEQ
Range: 1—1128 Mode: Normal
Codon Table: Universal
        E6/E7/E4 - SEQ ID Nos. 21 (DNA) and 22 (amino acid)

9               18              27              36              45              54
5'      ATG GAA AGT GCA AAT GCC TCC ACG TCT GCA ACG ACC ATA GAC CAG TTG TGC AAG
        Met Glu Ser Ala Asn Ala Ser Thr Ser Ala Thr Thr Ile Asp Gln Leu Cys Lys
                    63              72              81              90              99              108
        ACG TTT AAT CTA TCT ATG CAT ACG TTG CAA ATT AAT TGT GTG TTT TGC AAG AAT
        Thr Phe Asn Leu Ser Met His Thr Leu Gln Ile Asn Cys Val Phe Cys Lys Asn
                    117             126             135             144             153             162
        GCA CTG ACC ACA GCA GAG ATT TAT TCA TAT GCA TAT AAA CAC CTA AAG GTC CTG
        Ala Leu Thr Thr Ala Glu Ile Tyr Ser Tyr Ala Tyr Lys His Leu Lys Val Leu
                    171             180             189             198             207             216
        TTT CGA GGC TAT CCA TAT GCA GCC TGC GCG TGC CTA GAA TTT CAT GGA
        Phe Arg Gly Gly Tyr Pro Tyr Ala Ala Cys Ala Cys Leu Glu Phe His Gly
                    225             234             243             252             261             270
        AAA ATA AAC CAA TAT AGA CAC TTT GAT TAT GCT GGA TAT GCA ACA ACA GTT GAA
        Lys Ile Asn Gln Tyr Arg His Phe Asp Tyr Ala Gly Tyr Ala Thr Thr Val Glu
                    279             288             297             306             315             324
        GAA GAA ACT AAA CAA GAC ATC TTA GAC GTG CTA ATT CGG TGC TAC CTG TGT CAC
        Glu Glu Thr Lys Gln Asp Ile Leu Asp Val Leu Ile Arg Cys Tyr Leu Cys His
                    333             342             351             360             369             378
        AAA CCG CTG TGT GAA GTA GAA AAG GTA AAA CAT ATA CTA ACC AAG GCG CGG TTC
        Lys Pro Leu Cys Glu Val Glu Lys Val Lys His Ile Leu Thr Lys Ala Arg Phe
                    387             396             405             414             423             432
        ATA AAG CTA AAT TGT ACG TGG AAG GGT CGC TGC CTA CAC TGC TGG ACA ACA TGC
        Ile Lys Leu Asn Cys Thr Trp Lys Gly Arg Cys Leu His Cys Trp Thr Thr Cys
                    441             450             459             468             477             486
        ATG GAA GAC ATG TTA CCC AAG CTT CAT GGA AGA CAT GTT ACC CTA AAG GAT ATT
        Met Glu Asp Met Leu Pro Lys Leu His Gly Arg His Val Thr Leu Lys Asp Ile
                    495             504             513             522             531             540
        GTA TTA GAC CTG CAA CCT CCA GAC CCT GTA GGG TTA CAT TGC TAT GAG CAA TTA
        Val Leu Asp Leu Gln Pro Pro Asp Pro Val Gly Leu His Cys Tyr Glu Gln Leu
                    549             558             567             576             585             594
        GTA GAC AGC TCA GAA GAT GAG GTG GAC GAA GTG GAC GGA CAA GAT TCA CAA CCT
        Val Asp Ser Ser Glu Asp Glu Val Asp Glu Val Asp Gly Gln Asp Ser Gln Pro
                    603             612             621             630             639             648
        TTA AAA CAA CAT TTC CAA ATA GTG ACC TGT TGC TGT GGA TGT GAC AGC AAC GTT
        Leu Lys Gln His Phe Gln Ile Val Thr Cys Cys Cys Gly Cys Asp Ser Asn Val
                    657             666             675             684             693             702
        CGA CTG GTT GTG CAG TGT ACA GAA ACA GAC ATC AGA GAA GTG CAA CAG CTT CTG
        Arg Leu Val Val Gln Cys Thr Glu Thr Asp Ile Arg Glu Val Gln Gln Leu Leu
                    711             720             729             738             747             756
        TTG GGA ACA CTA AAC ATA GTG TGT CCC ATC TGC GCA CCG AAG ACC CCA TGG TCT
        Leu Gly Thr Leu Asn Ile Val Cys Pro Ile Cys Ala Pro Lys Thr Pro Trp Ser
                    765             774             783             792             801             810
        AGA GAG CTC GGT ACC ACT AAT GGA GCA CCA AAC ATT GGG AAG TAT GTT ATG GCA
        Arg Glu Leu Gly Thr Thr Asn Gly Ala Pro Asn Ile Gly Lys Tyr Val Met Ala
                    819             828             837             846             855             864
```

-continued

```
    GCA CAG TTA TAT GTT CTC CTG CAT CTG TAT CTA GCA CTA CAC AAG AAG TAT CCA
    --- --- --- --- --- --- --- --- --- --- --- --- --- --- --- --- --- ---
    Ala Gln Leu Tyr Val Leu Leu His Leu Tyr Leu Ala Leu His Lys Lys Tyr Pro
            873         882         891         900         909         918
    TTC CTG AAT CTA CTA CAT ACA CCC CCG CAC AGA CCT CCA CCC TTG TGT CCT CAA
    --- --- --- --- --- --- --- --- --- --- --- --- --- --- --- --- --- ---
    Phe Leu Asn Leu Leu His Thr Pro Pro His Arg Pro Pro Pro Leu Cys Pro Gln
            927         936         945         954         963         972
    GCA CCA AGG AAG ACG CAG TGC AAA CGC CGC CTA GGA AAC GAG CAC GAG GAG TCC
    --- --- --- --- --- --- --- --- --- --- --- --- --- --- --- --- --- ---
    Ala Pro Arg Lys Thr Gln Cys Lys Arg Arg Leu Gly Asn Glu His Glu Glu Ser
            981         990         999        1008        1017        1026
    AAC AGT CCC CTT GCA ACG CCT TGT GTG TGG CCC ACA TTG GAC CCG TGG ACA GTG
    --- --- --- --- --- --- --- --- --- --- --- --- --- --- --- --- --- ---
    Asn Ser Pro Leu Ala Thr Pro Cys Val Trp Pro Thr Leu Asp Pro Trp Thr Val
           1035        1044        1053        1062        1071        1080
    GAA ACC ACA ACC TCA TCA CTA ACA ATC ACG ACC AGC ACC AAA GAC GGA ACA ACA
    --- --- --- --- --- --- --- --- --- --- --- --- --- --- --- --- --- ---
    Glu Thr Thr Thr Ser Ser Leu Thr Ile Thr Thr Ser Thr Lys Asp Gly Thr Thr
           1089        1098        1107        1116        1125
    GTA ACA GTT CAG CTA CGC CTA AGA TCT CAT CAC CAT CAC CAT CAC TAA 3'
    --- --- --- --- --- --- --- --- --- --- --- --- --- --- --- ---
    Val Thr Val Gln Leu Arg Leu Arg Ser His His His His His His ***
File: CSL673.DNA
Range: 1-1398 Mode: Normal
Codon Table: Universal
        E6/E7/E5a/E4 - SEQ ID Nos. 23 (DNA) and 24 (amino acid)

9          18          27          36          45          54
5'  ATG GAA AGT GCA AAT GCC TCC ACG TCT GCA ACG ACC ATA GAC CAG TTG TGC AAG
    --- --- --- --- --- --- --- --- --- --- --- --- --- --- --- --- --- ---
    Met Glu Ser Ala Asn Ala Ser Thr Ser Ala Thr Thr Ile Asp Gln Leu Cys Lys
             63          72          81          90          99         108
    ACG TTT AAT CTA TCT ATG CAT ACG TTG CAA ATT AAT TGT GTG TTT TGC AAG AAT
    --- --- --- --- --- --- --- --- --- --- --- --- --- --- --- --- --- ---
    Thr Phe Asn Leu Ser Met His Thr Leu Gln Ile Asn Cys Val Phe Cys Lys Asn
            117         126         135         144         153         162
    GCA CTG ACC ACA GCA GAG ATT TAT TCA TAT GCA TAT AAA CAC CTA AAG GTC CTG
    --- --- --- --- --- --- --- --- --- --- --- --- --- --- --- --- --- ---
    Ala Leu Thr Thr Ala Glu Ile Tyr Ser Tyr Ala Tyr Lys His Leu Lys Val Leu
            171         180         189         198         207         216
    TTT CGA GGC GGT TAT CCA TAT GCA GCC TGC GCG TGC TGC CTA GAA TTT CAT GGA
    --- --- --- --- --- --- --- --- --- --- --- --- --- --- --- --- --- ---
    Phe Arg Gly Gly Tyr Pro Tyr Ala Ala Cys Ala Cys Cys Leu Glu Phe His Gly
            225         234         243         252         261         270
    AAA ATA AAC CAA TAT AGA CAC TTT GAT TAT GCT GGA TAT GCA ACA ACA GTT GAA
    --- --- --- --- --- --- --- --- --- --- --- --- --- --- --- --- --- ---
    Lys Ile Asn Gln Tyr Arg His Phe Asp Tyr Ala Gly Tyr Ala Thr Thr Val Glu
            279         288         297         306         315         324
    GAA GAA ACT AAA CAA GAC ATC TTA GAC GTG CTA ATT CGG TGC TAC CTG TGT CAC
    --- --- --- --- --- --- --- --- --- --- --- --- --- --- --- --- --- ---
    Glu Glu Thr Lys Gln Asp Ile Leu Asp Val Leu Ile Arg Cys Tyr Leu Cys His
            333         342         351         360         369         378
    AAA CCG CTG TGT GAA GTA GAA AAG GTA AAA CAT ATA CTA ACC AAG GCG CGG TTC
    --- --- --- --- --- --- --- --- --- --- --- --- --- --- --- --- --- ---
    Lys Pro Leu Cys Glu Val Glu Lys Val Lys His Ile Leu Thr Lys Ala Arg Phe
            387         396         405         414         423         432
    ATA AAG CTA AAT TGT ACG TGG AAG GGT CGC TGC CTA CAC TGC TGG ACA ACA TGC
    --- --- --- --- --- --- --- --- --- --- --- --- --- --- --- --- --- ---
    Ile Lys Leu Asn Cys Thr Trp Lys Gly Arg Cys Leu His Cys Trp Thr Thr Cys
            441         450         459         468         477         486
    ATG GAA GAC ATG TTA CCC AAG CTT CAT GGA AGA CAT GTT ACC CTA AAG GAT ATT
    --- --- --- --- --- --- --- --- --- --- --- --- --- --- --- --- --- ---
    Met Glu Asp Met Leu Pro Lys Leu His Gly Arg His Val Thr Leu Lys Asp Ile
            495         504         513         522         531         540
    GTA TTA GAC CTG CAA CCT CCA GAC CCT GTA GGG TTA CAT TGC TAT GAG CAA TTA
    --- --- --- --- --- --- --- --- --- --- --- --- --- --- --- --- --- ---
    Val Leu Asp Leu Gln Pro Pro Asp Pro Val Gly Leu His Cys Tyr Glu Gln Leu
            549         558         567         576         585         594
    GTA GAC AGC TCA GAA GAT GAG GTG GAC GAA GTG GAC GGA CAA GAT TCA CAA CCT
    --- --- --- --- --- --- --- --- --- --- --- --- --- --- --- --- --- ---
    Val Asp Ser Ser Glu Asp Glu Val Asp Glu Val Asp Gly Gln Asp Ser Gln Pro
            603         612         621         630         639         648
    TTA AAA CAA CAT TTC CAA ATA GTG ACC TGT TGC TGT GGA TGT GAC AGC AAC GTT
    --- --- --- --- --- --- --- --- --- --- --- --- --- --- --- --- --- ---
```

```
Leu Lys Gln His Phe Gln Ile Val Thr Lys Cys Cys Gly Cys Asp Ser Asn Val
        657         666         675         684         693             702
CGA CTG GTT GTG CAG TGT ACA GAA ACA GAC ATC AGA GAA GTG CAA CAG CTT CTG
--- --- --- --- --- --- --- --- --- --- --- --- --- --- --- --- --- ---
Arg Leu Val Val Gln Cys Thr Glu Thr Asp Ile Arg Glu Val Gln Gln Leu Leu
        711         720         729         738         747             756
TTG GGA ACA CTA AAC ATA GTG TGT CCC ATC TGC GCA CCG AAG ACC CCA TGG GAA
--- --- --- --- --- --- --- --- --- --- --- --- --- --- --- --- --- ---
Leu Gly Thr Leu Asn Ile Val Cy5 Pro Ile Cys Ala Pro Lys Thr Pro Trp Glu
        765         774         783         792         801             810
GTG GTG CCT GTA CAA ATA GCT GCA GGA ACA ACC AGC ACA TTC ATA CTG CCT GTT
--- --- --- --- --- --- --- --- --- --- --- --- --- --- --- --- --- ---
Val Val Pro Val Gln Ile Ala Ala Gly Thr Thr Ser Thr Phe Ile Leu Pro Val
        819         828         837         846         855             864
ATA ATT GCA TTT GTT GTA TGT TTT GTT AGC ATC ATA CTT ATT GTA TGG ATA TCT
--- --- --- --- --- --- --- --- --- --- --- --- --- --- --- --- --- ---
Ile Ile Ala Phe Val Val Cys Phe Val Ser Ile Ile Leu Ile Val Trp Ile Ser
        873         882         891         900         909             918
GAG TTT ATT GTG TAC ACA TCT GTG CTA GTA CTA ACA CTG CTT TTA TAT TTA CTA
--- --- --- --- --- --- --- --- --- --- --- --- --- --- --- --- --- ---
Glu Phe Ile Val Tyr Thr Ser Val Leu Val Leu Thr Leu Leu Leu Tyr Leu Leu
        927         936         945         954         963             972
TTG TGG CTG CTA TTA ACA ACC CCC TTG CAA TTT TTC CTA CTA ACT CTA CTT GTG
--- --- --- --- --- --- --- --- --- --- --- --- --- --- --- --- --- ---
Leu Trp Leu Leu Leu Thr Thr Pro Leu Gln Phe Phe Leu Leu Thr Leu Leu Val
        981         990         999        1008        1017            1026
TGT TAC TGT CCC GCA TTG TAT ATA CAC TAC TAT ATT GTT ACC ACA CAG CAA TCT
--- --- --- --- --- --- --- --- --- --- --- --- --- --- --- --- --- ---
Cys Tyr Cys Pro Ala Leu Tyr Ile His Tyr Tyr Ile Val Thr Thr Gln Gln Ser
       1035        1044        1053        1062        1071            1080
AGA GAG CTC GGT ACC ACT AAT GGA GCA CCA AAC ATT GGG AAG TAT GTT ATG GCA
--- --- --- --- --- --- --- --- --- --- --- --- --- --- --- --- --- ---
Arg Glu Leu Gly Thr Thr Asn Gly Ala Pro Asn Ile Gly Lys Tyr Val Met Ala
       1089        1098        1107        1116        1125            1134
GCA CAG TTA TAT GTT CTC CTG CAT CTG TAT CTA GCA CTA CAC AAG AAG TAT CCA
--- --- --- --- --- --- --- --- --- --- --- --- --- --- --- --- --- ---
Ala Gln Leu Tyr Val Leu Leu His Leu Tyr Leu Ala Leu His Lys Lys Tyr Pro
       1143        1152        1161        1170        1179            1188
TTC CTG AAT CTA CTA CAT ACA CCC CCG CAC AGA CCT CCA CCC TTG TGT CCT CAA
--- --- --- --- --- --- --- --- --- --- --- --- --- --- --- --- --- ---
Phe Leu Asn Leu Leu His Thr Pro Pro His Arg Pro Pro Pro Leu Cys Pro Gln
       1197        1206        1215        1224        1233            1242
GCA CCA AGG AAG ACG CAG TGC AAA CGC CGC CTA GGA AAC GAG CAC GAG GAG TCC
--- --- --- --- --- --- --- --- --- --- --- --- --- --- --- --- --- ---
Ala Pro Arg Lys Thr Gln Cys Lys Arg Arg Leu Gly Asn Glu His Glu Glu Ser
       1251        1260        1269        1278        1287            1296
AAC AGT CCC CTT GCA ACG CCT TGT GTG TGG CCC ACA TTG GAC CCG TGG ACA GTG
--- --- --- --- --- --- --- --- --- --- --- --- --- --- --- --- --- ---
Asn Ser Pro Leu Ala Thr Pro Cys Val Trp Pro Thr Leu Asp Pro Trp Thr Val
       1305        1314        1323        1332        1341            1350
GAA ACC ACA ACC TCA TCA CTA ACA ATC ACG ACC AGC ACC AAA GAC GGA ACA ACA
--- --- --- --- --- --- --- --- --- --- --- --- --- --- --- --- --- ---
Glu Thr Thr Thr Ser Ser Leu Thr Ile Thr Ser Thr Lys Asp Gly Thr Thr
       1359        1368        1377        1386        1395
GTA ACA GTT CAG CTA CGC CTA AGA TCT CAT CAC CAT CAC CAT CAC TAA 3'
--- --- --- --- --- --- --- --- --- --- --- --- --- --- --- ---
Val Thr Val Gln Leu Arg Leu Arg Ser His His His His His His ***
```

Junction of E1 and E4 ORFs for CSL791 and CSL762

SEQ ID Nos. 25 (DNA) and 26 (amino acid)

Modified
kpn1      Spe1
5' GAG GAA GAT GGA AGC AAT AGC CAA GCG TTT AGA TGC GTG CCA GGA ACA GTT GTT AGA ACT TTA GGT ACC ACT AAT GGA GCA CCA AAC ATT GGG AAG TAT GTT ATG GCA 3'
   Glu Glu Asp Gly Ser Asn Ser Gln Ala Phe Arg Cys Val Pro Gly Thr Val Val Arg Thr Leu Gly Thr Thr Asn Gly Ala Pro Asn Ile Gly Lys Tyr Val Met Ala
                              E1                                                                              E4

Junction of E5a and E1 for CSL762

SEQ ID Nos. 27 (DNA) and 28 (amino acid)

Xba1      Sac1
5' TGT CCC GCA TTG TAT ATA CAC TAC TAT ATT GTT ACC ACA CAG CAA TCT AGA GAG CTC GCG GAC GAT TCA GGT ACA GAA AAT GAG GGG TCT GGG TGT ACA GGA 3'
   Cys Pro Ala Leu Tyr Ile His Tyr Tyr Ile Val Thr Thr Gln Gln Ser Arg Glu Leu Ala Asp Asp Ser Gly Thr Glu Asn Glu Gly Ser Gly Cys Thr Gly
                          E5a                                                              E1

Junction of E7 and E1 for CSL791

SEQ ID Nos. 29 (DNA) and 30 (amino acid)

Nco1   Xba1    Sac1
5' TTG GGA ACA CTA AAC ATA GTG TGT CCC ATC TGC GCA CCG AAG ACC CCA TGG TCT AGA GAG CTC GCG GAC GAT TCA GGT ACA GAA AAT GAG GGG TCT GGG TGT ACA GGA 3'
   Leu Gly Thr Leu Asn Ile Val Cys Pro Ile Cys Ala Pro Lys Thr Pro Trp Ser Arg Glu Leu Ala Asp Asp Ser Gly Thr Glu Asn Glu Gly Ser Gly Cys Thr Gly
                              E7                                                              E1

Example 4

Preparation of Antibodies to HPV6b Early ORF Protein Products

The following peptides corresponding to portions of the sequence of the relevant E proteins, were synthesised and conjugated to diphtheria toxoid:

E6 dip.tox-CYRHFDYAQYATTVEEETKQDILD
E7 MHGRHVTLKDIVLDLQPPD-C-dip.tox

For the E6 peptide two rabbits (following prebleeding) were each inoculated with approximately 54 μg peptide/104 μg diphtheria toxoid in Freund's complete adjuvant followed at 3-weekly intervals by a similar dose of peptide conjugate in Freund's incomplete adjuvant. Bleeds were taken one week after the second dose and one week following the third dose. The same regime was used for the E7 peptide using 45 μg peptide/103 μg diphtheria toxoid.

Serum derived from the bleeds were tested for specific antibody in a solid phase EIA against biotin-conjugated peptide which had been bound to plates coated with strepavidin.

Example 5

Purification of Polyprotein E6/E7/E4

The trimer polyprotein E6/E7/E4 was expressed in *E. coli* BL21 cells by induction of cells at $OD_{600}$~1 using 0.4 mM IPTG. The cells were harvested by centrifugation (4,000 g, 20 minutes), resuspended in 30 mM Tris pH 8.0, disrupted by sonication (MSE, amplitude 18 μm, 4×30 seconds) and inclusion bodies pelleted by centrifugation (12,000 g, 30 minutes). The pellet containing the trimer was solubilized in 8 M Urea, 30 mM Tris pH 8.0 for 16 hours in the presence of protease inhibitors (Boehringer Cat. No. 1697498) and then centrifuged at 12,000 g for 30 minutes and the supernatant collected. To this, Tris2-carboxyethyl)phosphine TCEP) [Pierce] was added to 1,2 mM final concentration. The supernatant was applied to Q-sepharose HP (Pharmacia) and the column washed with one column volume of 8 M Urea, 1.2 mM TCEP, 30 mM Tris pH 8.0. Fractions were then eluted using a gradient containing 0 to 1 M NaCl in 10 column volumes of the washing buffer. The fractions obtained were examined by Western blot from 4 to 20% SDS-PAGE probed with the anti-E4 antibody MWE4.

Figure 11:
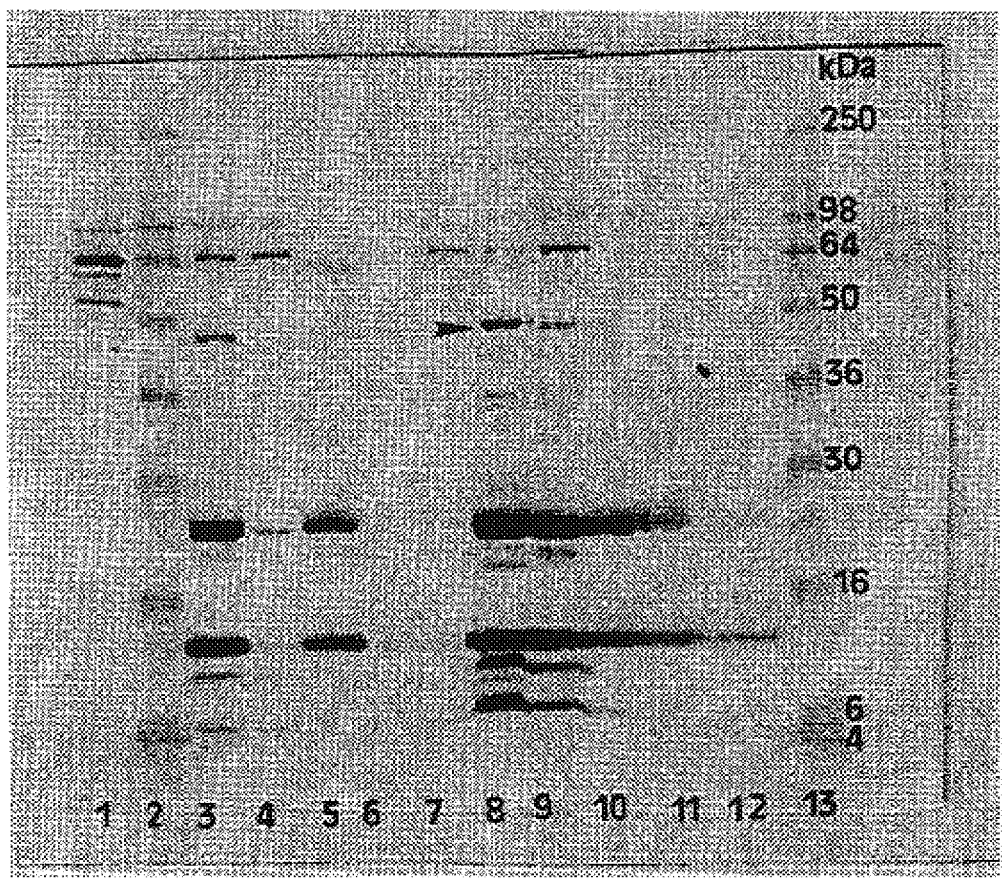

FIG. 11 shows a Western blot of material obtained from Q-sepharose. An immunoreactive band of ~41 kDa is evident in supernatant material from the urea solubilisation lane 3, and in fractions corresponding to 120 to 150 mM NaCl (lanes 8 and 9, arrow).

Supernatant from the urea solublisation was also applied to a column containing Chelating Sepharose Fast Flow (Pharmacia) to take advantage of the C-terminal six histidine sequence. Relatively poor binding of the trimer to the Nickel column was observed under the conditions described. The trimer was eluted from the column using a 0 to 500 mM imidazole gradient.

Example 6

In a further example of the present invention, a DNA sequence coding for a single polyprotein (FIG. 12) is formed by fusion of DNA fragments encoding HPV-6 early ORF proteins wherein the order of the ORFs is E2, E4, E5a, E5b, E6, E7 and E1.

The DNA sequences encoding the early ORF proteins are amplified individually by PCR using HPV-6 genomic DNA using the primers set out in Table 2.

TABLE 2

| Gene | | Oligonucleotides |
|---|---|---|
| E2 | (a) | 5'-GTG TGT GAG CTC ATG GAA GCA ATA GCC AAG-3' (SEQ ID No. 31) and |
| | (b) | 5'-GTG TGT GTC GAC CAA TAG GTG CAG TGA CAT-3' (SEQ ID No. 32) |
| E4 | (c) | 5'-GTG TGT GTC GAC ATG GGA GCA CCA AAC ATT-3' (SEQ ID No. 33) and |
| | | 5'-GTG TGT AGA TCT TAG GCG TAG CTG AAC TGT-3' (SEQ ID No. 34) |
| E5a | (e) | 5'-GTG TGT AGA TCT ATG GAA GTG GTG CCT GTA-3' (SEQ ID No. 35) and |
| | (f) | 5'-GTG TGT CTT AAG TTG CTG TGT GGT AAC AAT-3' (SEQ ID No. 36) |
| E5b | (g) | 5'-GTG TGT CTT AAG ATG ATG CTA ACA TGT CAA-3' (SEQ ID No. 37) and |
| | (h) | 5'-GTG TGT CCG CGG ATT CAT ATA TAT ATA ATC-3' (SEQ ID No. 38) |
| E6 | (i) | 5'-GTG TGT CCG CGG ATG GAA AGT GCA AAT GCC-3' (SEQ ID No. 39) and |
| | (j) | 5'-GTG TGT GCT AGC GGG TAA CAT GTC TTC CTA-3' (SEQ ID No. 40) |
| E7 | (k) | 5'-GTG TGT GCT AGC ATG CAT GGA AGA CAT GTT-3' (SEQ ID NO. 41) and |
| | (l) | 5'-GTG TGT CGA TCG GGT CTT CGG TGC GCA GAT-3' (SEQ ID No. 42) |
| E1 | (m) | 5'-GTG TGT CGA TCG ATG GCG GAC GAT TCA GGT-3' (SEQ ID No. 43) and |
| | (n) | 5'-GTG TGT GGT ACC TCA TAA AGT TCT AAC AAC-3' (SEQ ID No. 44) |

The primers are synthesised to incorporate artificial restriction enzyme sites at the 5' and 3' termini of the amplification products. These restriction enzyme sites are used to facilitate the fusion of PCR products encoding the appropriate early ORF proteins in the desired order and in the correct translational frame. The restriction enzyme sites are also used to aid the cloning of the PCR products into the expression vector pTrcHisA. When cloned into this vector, the polyprotein construct is expressed as an N-terminal hexaHis fusion. The nucleotide sequence and deduced amino acid sequence of this fusion are shown below (SEQ ID Nos. 45 and 46, respectively).

What is claimed is:

1. A nucleic acid molecule which encodes a polyprotein construct comprising at least two amino acid sequences fused directly or indirectly together, each of said sequences being the sequence of an early open reading frame (ORF) protein of papillomavirus (PV), or an immunogenic variant thereof, or a non-full length fragment that is a deletion mutant of the early ORF protein corresponding to at least 50% of the full length wild-type amino acid sequence, wherein i. said construct does not contain both an E6 and an E7 PV protein sequence;

ii. said construct does not contain an L2 PV protein sequence; and iii. when said construct consists of only two early ORF PV protein sequences, said protein sequences are from the same PV type.

2. A recombinant DNA molecule comprising an expression control sequence operatively linked to a nucleic acid molecule according to claim 1.

3. A recombinant DNA molecule according to claim 2, wherein said expression control sequence comprises promoter and initiator sequences, the sequence of nucleotides encoding the polyprotein construct being located in a single translational frame 3' to the promoter and initiator sequences, and a termination sequence located 3' to said sequence of nucleotides.

4. A recombinant DNA cloning vector comprising a recombinant DNA molecule according to claim 2.

5. A recombinant DNA cloning vector according to claim 4, wherein said vector is a plasmid.

6. A host cell transformed with a recombinant DNA molecule according to claim 2.

7. A host cell according to claim 6, wherein said host cell is E. coli.

8. A composition comprising a nucleic acid molecule according to claim 1, together with a pharmaceutically acceptable carrier and/or diluent.

9. A method for eliciting an immune response against PV in a host animal, which method comprises administering to the host animal an immunologically effective amount of a nucleic acid molecule according to claim 1.

10. A host cell according to claim 4, wherein said host cell is E. coli.

11. A nucleic acid molecule according to claim 1, wherein said sequences of said polyprotein construct are sequences of early ORF proteins of human Pv.

12. A nucleic acid molecule according to claim 11, wherein said early ORF sequences are selected from the group consisting of the E1, E2, E3, E4, E5 (E5a, E5b), E6, E7, and E8 proteins of PV.

13. A nucleic acid molecule according to claim 12, wherein said polyprotein construct is selected from the group consisting of:

a. E6/E4;
   b. E6/E5a/E4;
   c. E2/E5b;
   d. E2/E1/E5b;
   e. E2/E5a/E5b; and
   f. E2/E1/E5a/E5b.

14. A nucleic acid molecule according to claim 1, wherein said polyprotein construct further comprises one or more linker sequences between and/or before and/or after said amino acid sequences.

15. A nucleic acid molecule according to claim 14, wherein said linker sequence(s) comprise from 1 to 5 amino acid residues.

16. A nucleic acid molecule according to claim 1, wherein said polyprotein construct further comprises a tag protein or peptide moiety fused or otherwise coupled thereto.

17. A nucleic acid molecule according to claim 16, wherein said tag moiety is selected from the group consisting of $(His)_6$, glutathione-S-transferase (GST), and FLAG.

18. A nucleic acid molecule according to claim 1, wherein said polyprotein construct further comprises an adjuvant moiety fused or otherwise coupled thereto.

19. A nucleic acid molecule according to claim 18, wherein said adjuvant moiety is selected from the group consisting of diphtheria toxin, cholera toxin, E. coli heat labile toxin (LT), and a non-toxic derivative thereof.

20. A nucleic acid molecule according to claim 19, wherein said non-toxic derivative is selected from the group consisting of the holotoxoid of cholera toxin, the B-subunit of cholera toxin, the holotoxoid of LT, and the B-subunit of LT.

21. A nucleic acid molecule according to claim 1, wherein said polyprotein construct further comprises a lipid binding region.

22. A nucleic acid molecule according to claim 21, wherein said lipid binding region is an influenza haemagglutinin tail.

23. A nucleic molecule according to claim 22, wherein said lipid binding region is an influenza haemagglutinin tail.

* * * * *